(12) United States Patent  
Hatakeyama et al.

(10) Patent No.: US 9,074,994 B2  
(45) Date of Patent: Jul. 7, 2015

(54) INSPECTION METHOD AND APPARATUS OF A GLASS SUBSTRATE FOR IMPRINT

(75) Inventors: Masahiro Hatakeyama, Ohta-Ku (JP); Norio Kimura, Ohta-Ku (JP)

(73) Assignee: EBARA CORPORATION, Tokyo (JP)

( * ) Notice: Subject to any disclaimer, the term of this patent is extended or adjusted under 35 U.S.C. 154(b) by 248 days.

(21) Appl. No.: 12/500,308

(22) Filed: Jul. 9, 2009

(65) Prior Publication Data

US 2010/0012838 A1 Jan. 21, 2010

(30) Foreign Application Priority Data

Jul. 16, 2008 (JP) ................. 2008-185236

(51) Int. Cl.  
*G01N 23/00* (2006.01)  
*G01N 23/225* (2006.01)

(52) U.S. Cl.  
CPC .................. *G01N 23/2251* (2013.01)

(58) Field of Classification Search  
USPC ............... 250/306, 307, 308, 309, 310, 311; 430/299, 296  
See application file for complete search history.

(56) References Cited

U.S. PATENT DOCUMENTS

| | | | | |
|---|---|---|---|---|
| 4,417,203 | A * | 11/1983 | Pfeiffer et al. | 324/501 |
| 6,172,363 | B1 | 1/2001 | Shinada et al. | |
| 6,329,826 | B1 | 12/2001 | Shinada et al. | |
| 6,583,634 | B1 | 6/2003 | Nozoe et al. | |
| 6,803,571 | B1 * | 10/2004 | Mankos et al. | 850/9 |
| 6,930,309 | B1 * | 8/2005 | Mankos et al. | 850/9 |
| 7,115,354 | B2 * | 10/2006 | Hatakeyama et al. | 430/322 |
| 7,638,780 | B2 * | 12/2009 | Kilburn et al. | 250/492.1 |
| 7,816,655 | B1 * | 10/2010 | Hess et al. | 250/492.2 |
| 2002/0148989 | A1 * | 10/2002 | Imai | 250/591 |
| 2002/0190207 | A1 * | 12/2002 | Levy et al. | 250/306 |
| 2004/0169151 | A1 * | 9/2004 | Yagi et al. | 250/492.2 |
| 2004/0214502 | A1 * | 10/2004 | Kotsubo et al. | 445/49 |
| 2004/0266223 | A1 * | 12/2004 | Tanaka et al. | 438/795 |
| 2005/0084804 | A1 * | 4/2005 | Truskett et al. | 430/311 |
| 2005/0170621 | A1 * | 8/2005 | Kim et al. | 438/584 |
| 2005/0205781 | A1 * | 9/2005 | Kimba | 250/311 |
| 2006/0076509 | A1 * | 4/2006 | Okino et al. | 250/492.2 |
| 2006/0222968 | A1 * | 10/2006 | Talin et al. | 430/5 |
| 2007/0158589 | A1 * | 7/2007 | Bertsche et al. | 250/492.2 |
| 2007/0283832 | A1 * | 12/2007 | Hotelling | 101/487 |

(Continued)

FOREIGN PATENT DOCUMENTS

| | | |
|---|---|---|
| JP | 64-039021 A | 2/1989 |
| JP | 2005-533393 A | 11/2005 |

(Continued)

*Primary Examiner* — Nicole Ippolito  
*Assistant Examiner* — Jason McCormack  
(74) *Attorney, Agent, or Firm* — Westerman, Hattori, Daniels & Adrian, LLP

(57) ABSTRACT

A method for inspecting a glass substrate for imprint including a glass substrate with a pattern surface and a transmissive conductive film coating at least part of the pattern surface, includes an electron beam irradiation step of irradiating the pattern surface of the glass substrate for imprint disposed on a stage with an electron beam having a predetermined irradiation area; an electron detection step of simultaneously detecting electrons from the pattern surface by the electron beam irradiation by means of a detection surface with a plurality of pixels; and a defect detection step of obtaining an image of the pattern surface based on the electrons detected by the detection surface and detecting a defect of the pattern surface.

22 Claims, 17 Drawing Sheets

(56) References Cited

U.S. PATENT DOCUMENTS

| | | | |
|---|---|---|---|
| 2008/0054931 A1* | 3/2008 | Zhao et al. | 324/765 |
| 2008/0123089 A1* | 5/2008 | Seul et al. | 356/237.5 |
| 2008/0296496 A1* | 12/2008 | Zhao et al. | 250/307 |
| 2008/0296499 A1* | 12/2008 | Faber | 250/311 |
| 2009/0039290 A1* | 2/2009 | Prakash et al. | 250/492.1 |
| 2009/0092791 A1* | 4/2009 | Terasaki et al. | 428/156 |
| 2009/0101816 A1* | 4/2009 | Noji et al. | 250/310 |
| 2009/0146081 A1* | 6/2009 | Stark | 250/492.2 |
| 2010/0028682 A1* | 2/2010 | Shinohara | 428/409 |

FOREIGN PATENT DOCUMENTS

| | | |
|---|---|---|
| JP | 2007-281492 A | 10/2007 |
| JP | 2008-068612 A | 3/2008 |
| WO | 02/45153 A1 | 6/2002 |

* cited by examiner

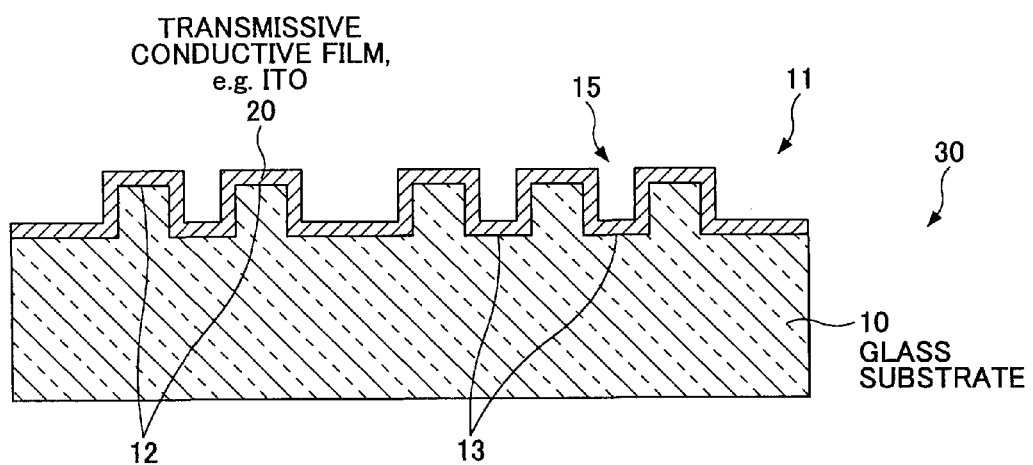
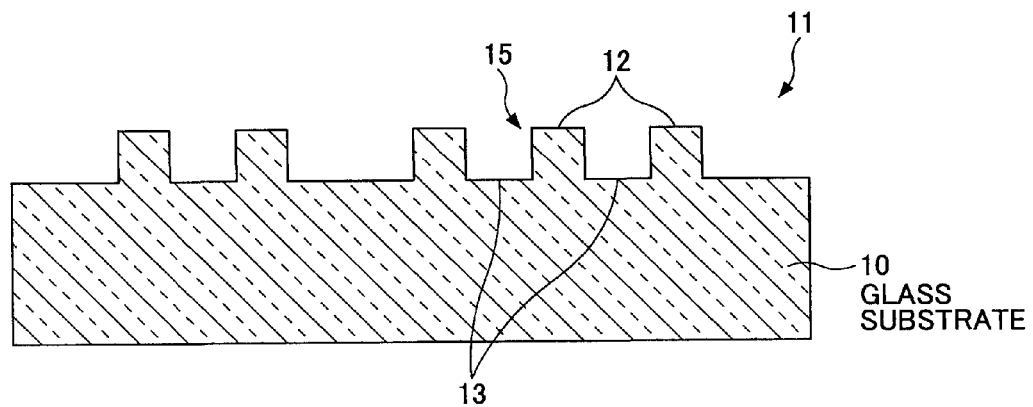

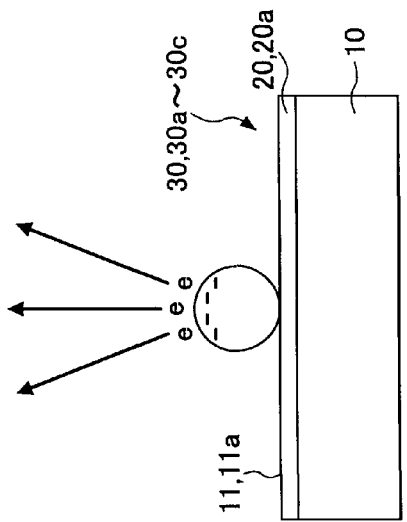
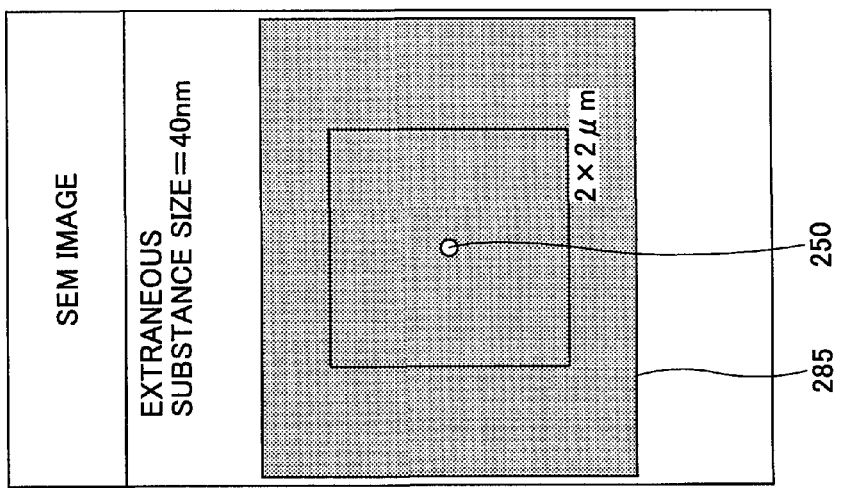
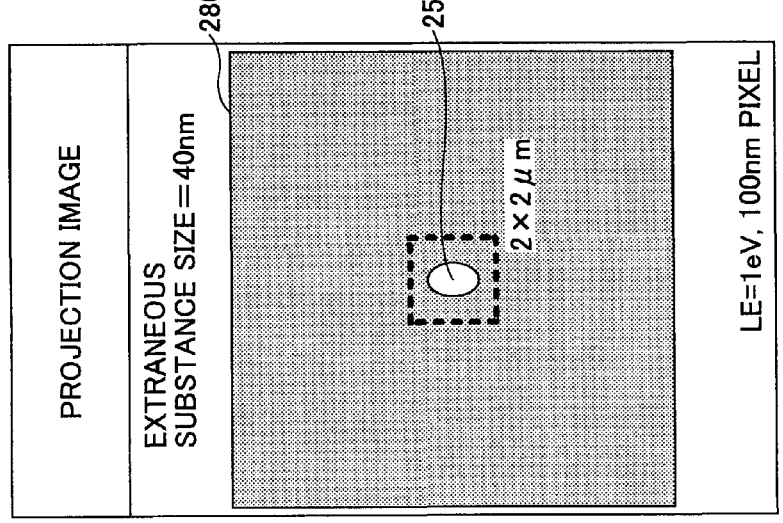

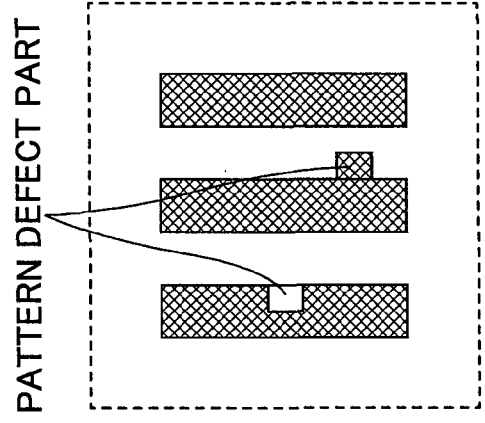
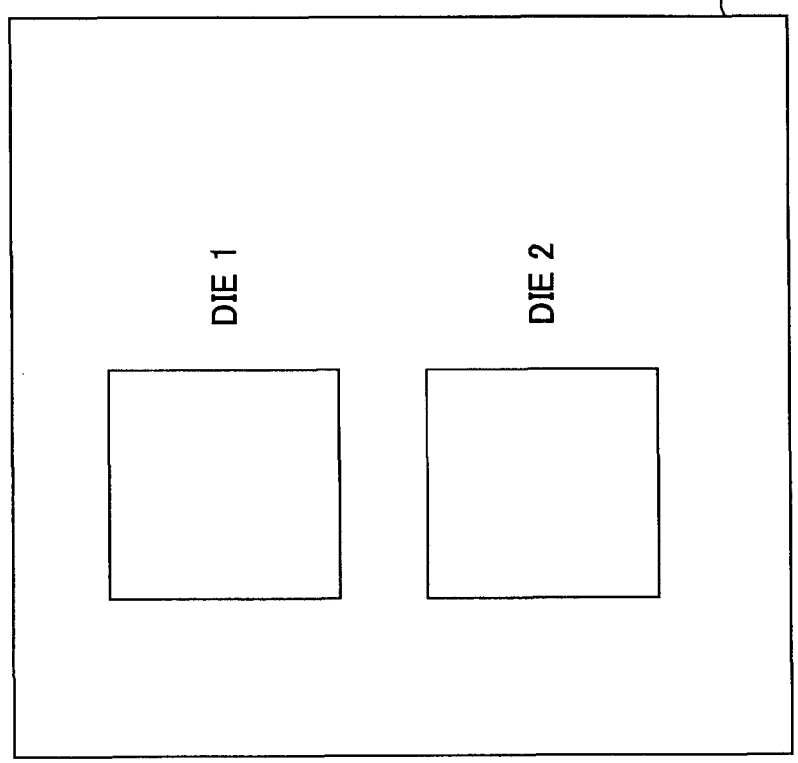
FIG.16A
FIG.16B

INSPECTION METHOD AND APPARATUS OF A GLASS SUBSTRATE FOR IMPRINT

CROSS-REFERENCE TO RELATED APPLICATIONS

This patent application is based upon and claims the benefit of priority of Japanese Patent Application No. 2008-185236 filed on Jul. 16, 2008, the entire contents of which are incorporated herein by reference.

BACKGROUND OF THE INVENTION

1. Field of the Invention

The present invention generally relates to an inspection method and apparatus of a glass substrate for imprint.

2. Description of the Related Art

Conventionally, as disclosed in Japanese patent publication No. 2008-68612, a nanoimprint mold is known. The nanoimprint mold includes a substrate, a pattern part with a concave-convex pattern formed on the substrate, a hard layer made of harder materials than the pattern part and formed on the surface of the pattern part, and a demolding layer formed on the surface of the hard layer. Each layer of the nanoimprint mold includes effective materials suitable for its respective role and lamination of the layers constitutes the nanoimprint mold. The nanoimprint mold is intended to be able to uniformly transfer an original pattern even to a flexible substrate, to prevent damage by pressure and contamination by resin, to enhance accuracy of a transferred pattern, and to improve durability.

The pattern part of the nanoimprint mold is constructed of flexible materials and is formed in a deformable state in order to be available for the flexible substrate. The hard layer of the nanoimprint mold is formed of an oxide film such as Si oxide (for example, $SiO_2$) or ITO (i.e., Indium Tin Oxide) in order to enhance durability and accuracy of the transferred pattern. The demolding layer of the nanoimprint is formed of an organic molecular film to facilitate separation between polymer thin films on which nanoscale structures are impressed.

In addition, when an inspection to detect a pattern defect of the nanoimprint mold as disclosed in the Japanese patent publication No. 2008-68612, or an extraneous substance on a surface of a pattern part is performed, an inspection method by light is common. More specifically, a surface image of the nanoimprint mold is obtained by way of a dark-field light scattering method, and the pattern defect or the extraneous substance is detected.

However, the conventional inspection method by light has insufficient detection sensitivity for the nanoimprint mold disclosed in the Japanese patent publication No. 2008-68612. More specifically, in the inspection method by light, the detection sensitivity extremely decreases for the ultra fine pattern, and attachment of the extraneous substance or an organic substance whose size is less than 50 to 100 nm. Hence, the inspection method by light becomes difficult to apply to the minute scale objects. A major factor of this is considered to arise from the size of the pattern and the extraneous substance smaller than a wavelength of the light, which decreases a signal-to-noise (signal/noise) ratio.

As another inspection method, a defect inspection method by SEM (i.e., Scanning Electron Microscope) using a more sensitive electron beam than the light is possible. For example, the SEM inspection method makes it possible to use a smaller pixel size than the size of an inspection object by focusing the electron beam and to inspect the extraneous substance with high resolution. According to the SEM inspection method, the inspection of the nanoimprint mold disclosed in the Japanese patent publication No. 2008-68612 is possible. However, because of the small pixel size, the SEM inspection method needs an enormous amount of inspection time and the inspection in a practical time is difficult, which makes the SEM inspection method impractical. Moreover, when the nanoimprint mold is irradiated with the electron beam, charging becomes prominent and the appropriate pattern image cannot be obtained because the nanoimprint mold is entirely formed of insulation materials such as glass.

SUMMARY OF THE INVENTION

Accordingly, embodiments of the present invention may provide a novel and useful inspection method and apparatus of a glass substrate for imprint solving one or more of the problems discussed above.

More specifically, the embodiments of the present invention may provide an inspection and apparatus of a glass substrate for imprint whereby high-sensitivity, high-speed and high-throughput inspection can be realized with respect to a pattern and an extraneous substance with the ultra fine size less than 50 to 100 nm.

One aspect of the present invention may be to provide a method for inspecting a glass substrate for imprint, the glass substrate for imprint including, a glass substrate with a pattern surface including a fine pattern for imprint; and a transmissive conductive film coating at least part of the pattern surface, the method including:

an electron beam irradiation step of irradiating the pattern surface of the glass substrate for imprint disposed on a stage with an electron beam having a predetermined irradiation area;

an electron detection step of simultaneously detecting electrons from the pattern surface by the electron beam irradiation by means of a detection surface with a plurality of pixels; and a defect detection step of obtaining an image of the pattern surface based on the electrons detected by the detection surface and detecting a defect of the pattern surface.

Another aspect of the present invention may be to provide an inspection apparatus to inspect a glass substrate for imprint, the glass substrate for imprint including, a glass substrate with a pattern surface including a fine pattern for imprint; and a transmissive conductive film coating at least part of the pattern surface, the apparatus including:

an electron gun configured to irradiate the pattern surface of the glass substrate for imprint disposed on a stage with an electron beam having a predetermined irradiation area;

a detector configured to simultaneously detect electrons from the pattern surface by the electron beam irradiation by means of a detection surface with a plurality of pixels; and a defect detection unit configured to obtain an image of the pattern surface based on the electrons detected by the detection surface of the detector and to detect a defect of the pattern surface.

Additional objects and advantages of the embodiments are set forth in part in the description which follows, and in part will become obvious from the description, or may be learned by practice of the invention. The object and advantages of the invention will be realized and attained by means of the elements and combinations particularly pointed out in the appended claims. It is to be understood that both the foregoing general description and the following detailed description are exemplary and explanatory and are not restrictive of the invention as claimed.

BRIEF DESCRIPTION OF THE DRAWINGS

FIG. 1 is a view showing an example of a cross-sectional configuration of a glass substrate for imprint of a first embodiment of the present invention;

FIG. 2 is a view showing a cross-sectional configuration of a glass substrate of the glass substrate for imprint;

FIG. 12A is a view showing an image of an extraneous substance obtained by an inspection method and apparatus of the fifth embodiment of the present invention;

FIG. 12B is a view showing an image of the extraneous substance obtained by a conventional inspection apparatus;

FIG. 12C is a lateral view showing a state where the extraneous substance is on a glass substrate for imprint;

FIG. 16A is a view showing an example where there are a plurality of dies;

FIG. 16B is a view showing an example of a die pattern and die pattern defects;

DETAILED DESCRIPTION OF THE PREFERRED EMBODIMENTS

Figure 3A:
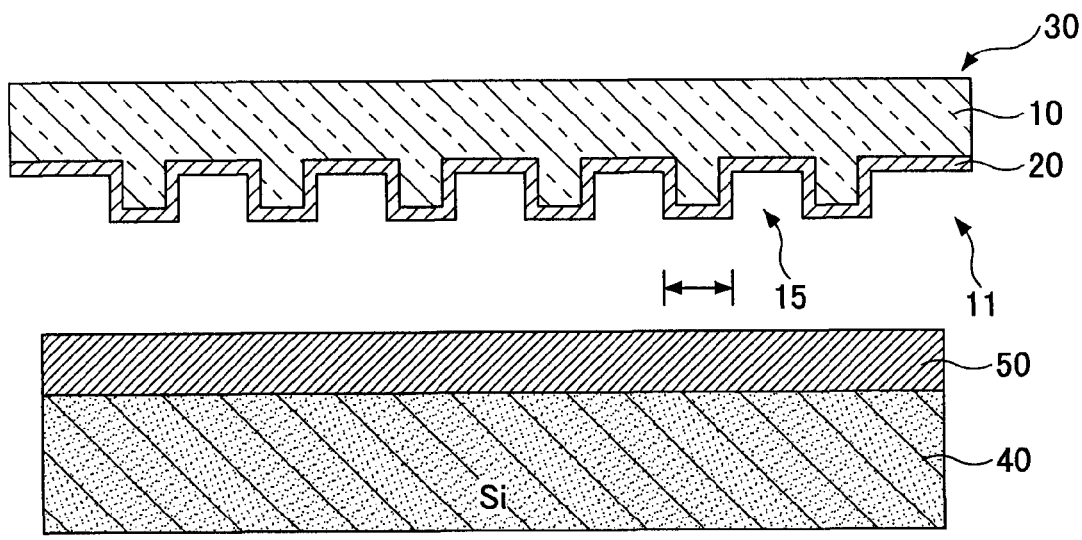
FIG. 3A is a first view showing a resist pattern forming process of preparing a silicon substrate and a glass substrate for imprint.

A description is given below, with reference to FIGS. 1 through 18 of embodiments of the present invention.

Embodiment 1

FIG. 1 is a view showing an example of a cross-sectional configuration of a glass substrate for imprint 30 of a first embodiment of the present invention. The glass substrate for imprint 30 includes a glass substrate 10 and a transmissive conductive film 20 coating a surface of the glass substrate 10.

The glass substrate 10 is a substrate including a transmissive glass material that transmits light. Various kinds of glasses are available for the glass substrate 10, including a transparent glass material. For example, quartz glass is available for the glass substrate 10. A pattern surface 11 with a fine pattern 15 is formed on a surface of the glass substrate 10. For example, the fine pattern 15 may be a configuration pattern including a concave-convex pattern. In FIG. 1, convex parts 12 and concave parts 13 are formed on the surface of the glass substrate 10 and constitute the pattern surface 11 including the fine pattern 15 of a concave-convex configuration. The fine pattern 15 may include a nanometer-level pattern. For example, a width of the fine pattern 15 may be between 10 and 20 nm, between 10 and 50 nm or between 10 and 100 nm.

The pattern surface 11 of the glass substrate 10 is coated with the transmissive conductive film 20. The whole area of the pattern surface 11 of the glass substrate 10 is coated with the transmissive conductive film 20 and the whole fine pattern 15 is coated with transmissive conductive film 20. The transmissive conductive film 20 is a transmissive and conductive film that transmits light and electricity, including a transparent conductive film. For example, a coating thickness of the transmissive conductive film is controlled in a range of 0.1 to 10 nm. A resistance value of the transmissive conductive film 20 may be about from 100 to 1000 μΩ-cm and an ultraviolet transmittance may be about 70 percent.

For example, ITO (i.e., Indium Tin Oxide) film is available for the transmissive conductive film 20. ITO film generally includes indium oxide to which tin oxide of 5 to 10 wt percent is added. Also, tin oxide or zinc oxide is available for the transmissive conductive film 20. In the fabrication process of the glass substrate for imprint 10 of the first embodiment, the fine pattern 15 of the glass substrate 10 is formed, and then the transmissive conductive film 20 is formed on the fine pattern 15.

FIG. 2 is a view showing a cross-sectional configuration of the glass substrate 10 of the glass substrate for imprint 30 of the first embodiment. As explained in FIG. 1, the glass substrate 10 includes the pattern surface 11 with a fine pattern 15 on either surface. Conventionally, only the glass substrate 10 is used as a glass substrate for imprint as it is. In contrast, the glass substrate for imprint 30 explained in FIG. 1 allows the surface of the pattern surface 11 to have conductivity and keeps transparency of the glass substrate 10 because the whole area of the pattern surface 11 is coated with the transmissive conductive film 20.

FIG. 3 is a view showing a fabrication process to form a resist pattern on a silicon substrate 40 using the glass substrate for imprint 30 of the first embodiment.

FIG. 3A is a view showing a process preparing the silicon substrate 40 and the glass substrate for imprint 30. A resist film 50 is formed on either entire surface of the silicon substrate 40. By forming a resist pattern on the resist film 50, a desired pattern can be formed on the silicon substrate 40 in a following etching process.

On the other hand, in FIG. 3A, the glass substrate for imprint 30 of the embodiment 1 is prepared by facing the pattern surface 11 toward the resist film 50, over the silicon substrate 40 coated with the resist film 50. By transferring the fine pattern 15 formed on the pattern surface 11 of the glass substrate for imprint 30 to the resist film 50, a predetermined pattern can be formed in the resist film 50.

Figure 3B:
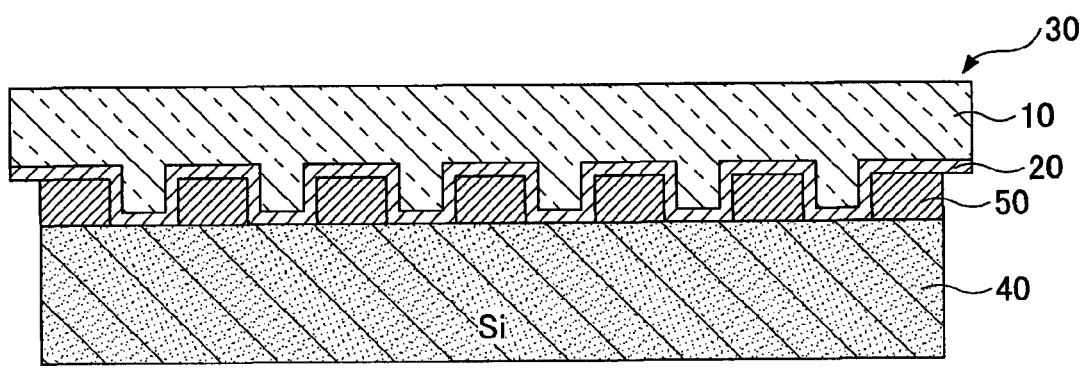
FIG. 3B is a second view showing a resist pattern forming process of pressing a pattern surface against a resist film.

FIG. 3B is a view showing a process pressing the pattern surface 11 of the glass substrate for imprint 30 against the resist film 50 on the silicon substrate 40. In FIG. 3B, the glass substrate for imprint 30 is pressed against the resist film 50 so as to reach the silicon substrate 40. By doing this, the resist film 50 is transformed into a pattern configuration according to the shaped pattern surface 11 of the glass substrate for imprint 30, and the fine pattern 15 is transferred to the resist film 50.

Figure 3C:
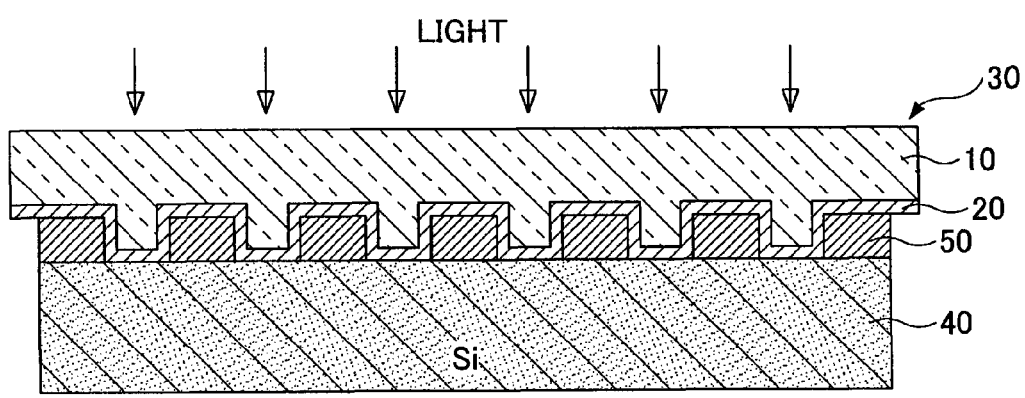
FIG. 3C is a third view showing a resist pattern forming process of irradiating the pattern surface with light.

FIG. 3C is a view showing a process irradiating a silicon substrate 40 with light through the glass substrate for imprint 30. Because the glass substrate 10 making up the glass substrate for imprint 30 is transmissive and the transmissive conductive film 50 is also transmissive, an incident light from the back side of the glass substrate for imprint 30 (i.e., opposite surface of the pattern surface 11) goes through the glass substrate for imprint 30, reaches the resist film 50 and hardens the resist film 50. Various kinds of lights are available for the light as long as the light can harden the resist film 50. For example, ultraviolet light is available for the light. The resist film 50 includes materials that become hardened when irradiated with the light such as the ultraviolet light.

Figure 3D:
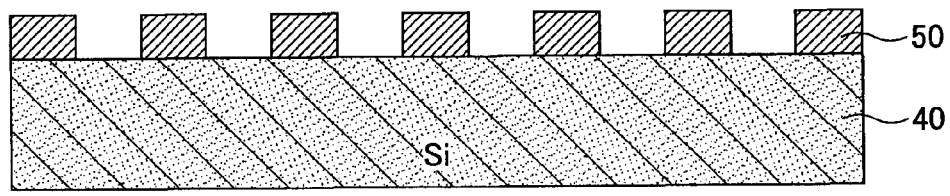
FIG. 3D is a fourth view showing a resist pattern forming process of detaching the glass substrate for imprint from the resist film.

FIG. 3D is a view showing a process detaching the glass substrate for imprint 30 from the resist film 50 of the silicon substrate 40. When the glass substrate for imprint 30 is detached from the silicon substrate 40 after the ultraviolet light irradiation, a predetermined resist pattern is formed on the silicon substrate 40. With the resist pattern, it is possible to form a pattern configuration including a desired concave-convex fine pattern 15 on the silicon substrate 40 in the following etching process. In FIG. 3A through FIG. 3D, the silicon substrate 40 is given as an example of a substrate of a resist pattern forming object, but the resist pattern forming method of the embodiment is applicable to other kinds of substrates, as long as a surface of the substrates can be coated with the resist film 50.

In this way, the resist pattern forming method of the embodiment can be conducted in a similar way of the usual fabrication process of the glass substrate for imprint, by using the glass substrate for imprint 30 of the first embodiment. Hence, in order to form the resist pattern including the high-accuracy fine pattern 15 in the resist film 50 on the silicon substrate 40, it is necessary to form the fine pattern 15 formed on the silicon substrate 40 with high accuracy.

More specifically, in this process, an inspection of the glass substrate for imprint 30 is necessary before a pattern transfer by pressing the glass substrate for imprint 30 to a surface of the resist film 50. If there is a pattern defect or an extraneous substance on the glass substrate for imprint 30, a transferred resist pattern may include a pattern defect configuration deformed from a normal pattern. Moreover, if there is an extraneous substance on the glass substrate for imprint 30, the extraneous substance prevents the normal pattern from being transferred to the resist film 50. Also, the extraneous substance causes deformation of the resist pattern in a thickness direction. If a wafer is etched using the resist pattern including the deformation, only a part corresponding to the deformation is deeply etched, which causes a defect such as a pinhole. In this manner, if there is the defect of the fine pattern 15 of the glass substrate for imprint 30 or the extraneous substance, as a result, a normal semiconductor structure including LSI (i.e., Large Scale integration) cannot be formed, and a produced semiconductor becomes a defective product.

Thus, a defect inspection of the glass substrate for imprint 30 is important. Because the pattern configuration of nanometer-level is transferred to the resist film 50 without change in the pattern transfer by imprint, a pattern size becomes less than or equal to 100 nm. For example, each line and space width of L/S (i.e., Line/Space) becomes less than or equal to 100 nm. However, in a fine pattern shorter than a wavelength of light, an inspection by light inspection apparatus becomes difficult because a required resolution of light is impossible to obtain, and an inspection by a defect inspection apparatus using an electron beam is more effective. In particular, a projection-type electron beam defect inspection apparatus is a suitable device to inspect the fine pattern 15 and the fine extraneous substance at high speed and with high resolution because the projection-type electron beam defect inspection apparatus can continuously take a two-dimensional image. However, the projection-type electron beam defect inspection apparatus has a problem that an obtained image is unstable when there is surface electric potential fluctuation by charging. Thus, it is difficult for the projection-type electron beam defect inspection apparatus to image the glass substrate 10 of an insulator. To solve the problem, in the embodiment, the pattern surface 11 of the glass substrate 10 is coated with the transmissive conductive film 20. This makes the surface electric potential of the glass substrate 10 stable and allows the projection-type electron beam defect inspection apparatus to obtain a stable electron image. A specific inspection method and an apparatus configuration are described later.

Figure 4:
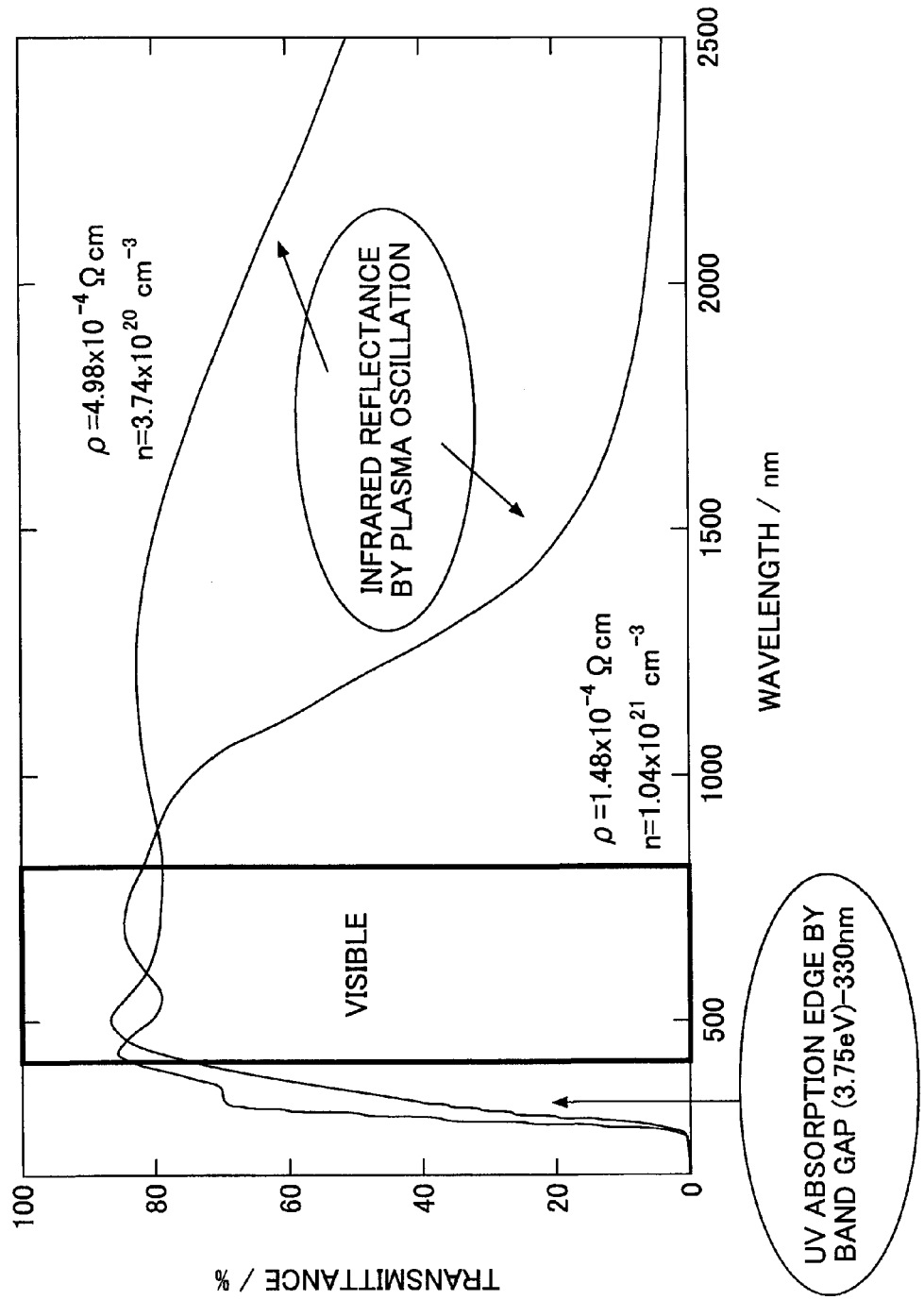
FIG. 4 is a view showing an example of a transmittance characteristic of a transmissive conductive film.

FIG. 4 is a view showing an example of a transmittance characteristic of the transmissive conductive film 20 used for the glass substrate for imprint 30 of the embodiment. Usually, metal reflects light (more specifically, visible light), but as shown in FIG. 4, the transmissive conductive film 20 shows a transmittance of 80 percent in the visible light range (which is shown by the word "Visible" in FIG. 4). Thus, the glass substrate for imprint 30 of the embodiment causes the pattern surface 11 to be conductive without decreasing the transmittance. In FIG. 4, the transmissive conductive film 20 also shows a high transmittance in an ultraviolet light range with a little shorter wavelength than in the visible light range. Thus, the glass substrate for imprint 30 of the embodiment is available for the ultraviolet light as well as the visible light. Hence, the resist film 50 can be hardened by using the ultraviolet light, and a high-accuracy resist pattern can be formed.

Thus, because the transmissive conductive film 20 is transmissive, the glass substrate for imprint 30 can function as a proper mask, and the resist pattern formation to the resist film 50 on the other substrate can be performed with high accuracy.

In addition, causing the pattern surface 11 to be conductive allows inspecting the pattern surface with a variety of electron beams. In general, by irradiating a sample such as a substrate with an electron beam, and by detecting electrons generated from the sample, an image of a surface of the sample is obtained with a much higher accuracy than the light irradiation inspection. Thus, the inspection by the electron beam is more preferable than the inspection by the light when the fine pattern 15 is nanometer-level, but the inspection by the electron beam cannot obtain a proper surface image when the sample is electrostatically charged. Charging of the sample tends to occur when the sample is an insulator. Therefore, even though the glass substrate 10 is made of an insulator that is a material likely to be charged, coating the pattern surface 11 of an inspection object with the transmissive conductive film 20 makes the charging less likely to occur, shown by the glass substrate for imprint 30 of the embodiment. This makes it possible to inspect the pattern surface 11 with high accuracy using the electron beam. This high-accuracy inspection further makes it possible to form the fine pattern 15 with high accuracy. Thus, the glass substrate for imprint 30 enables a high-accuracy defect inspection using the electron beam. Moreover, since the imprint is performed by using the glass substrate for imprint 30 with a high-accuracy pattern by the proper inspection, a high-accuracy resist pattern can be formed on a substrate of a fabrication object.

In addition, in the fabrication method of the glass substrate for imprint 30 of the first embodiment, for example, the glass substrate for imprint 30 can be produced by coating the whole pattern surface 11 including the fine pattern 15 of the glass substrate 10 in a state shown in FIG. 2, with the transmissive conductive film 20 by vapor deposition. For example, it is possible to put the glass substrate 10 in a process chamber and to evaporate the transmissive conductive film 20 by CVD (i.e., Chemical Vapor Deposition). This makes it possible to form the transmissive conductive film 20 on the entire pattern surface 11 of the glass substrate 10. Also, forming the transmissive conductive film 20 by plating is possible. For example, it is possible to immerse the glass substrate 10 in a plating chamber filled with a plating liquid and to form the transmissive conductive film 20 by electroplating or electroless plating.

According to the glass substrate for imprint 30, coating the entire pattern surface 11 of the transmissive conductive film 20 allows a surface electric potential to be stable and enables the high-accuracy inspection of the pattern surface 11 by the electron beam to be performed by preventing charging from occurring.

Embodiment 2

Figure 5:
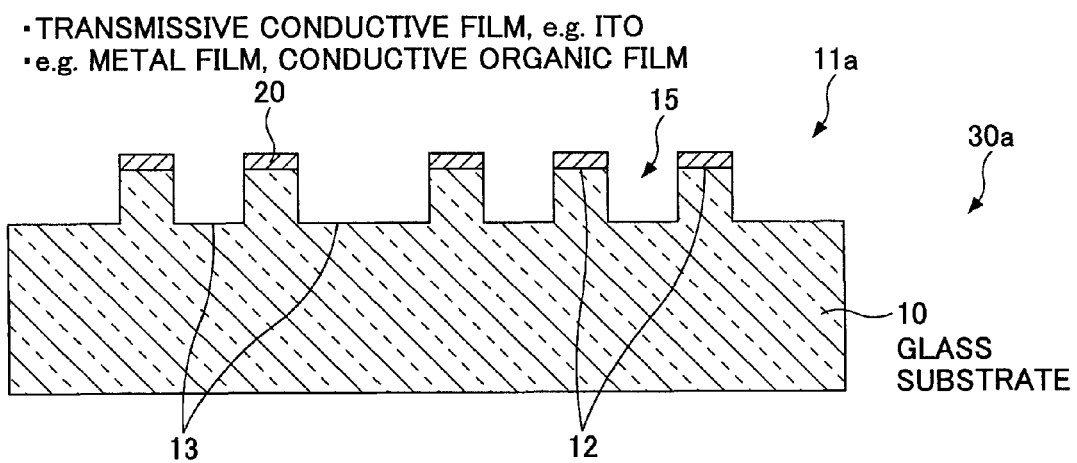
FIG. 5 is a view showing an example of a cross-sectional configuration of a glass substrate for imprint of a second embodiment of the present invention.

FIG. 5 is a view showing an example of a cross-sectional configuration of a glass substrate for imprint 30a of a second embodiment of the present invention. In FIG. 5, the glass substrate for imprint 30a of the second embodiment is similar to the glass substrate for imprint 30 of the first embodiment regarding the pattern surface 11a of a glass substrate 10 coated with a transmissive conductive film 20. However, the glass substrate for imprint 30a differs from the glass substrate for imprint 30 of the first embodiment in that the transmissive conductive films 20 are not formed on the whole area of the pattern surface but formed on only convex parts 12 of a fine pattern 15. Thus, coating only a part of the pattern surface 11a, not the whole area of the pattern surface 11a, is possible. For example, coating only the convex parts 12 is possible. Because a pattern width of the fine pattern 15 is very minute such as 10 to 20 nm, it is thought that even forming the transmissive conductive film 20 only on the convex parts 12 can enhance conductivity of the pattern surface 11a made of the glass substrate 10 of an insulator, which results in a great effect to prevent charging during the inspection.

FIGS. 6A through 6D and FIGS. 7A through 7C are views showing a fabrication process of the glass substrate for imprint 30a of the second embodiment. FIGS. 6A through 6D are views showing processes until resist formation of the glass substrate for imprint 30a.

Figure 6A:
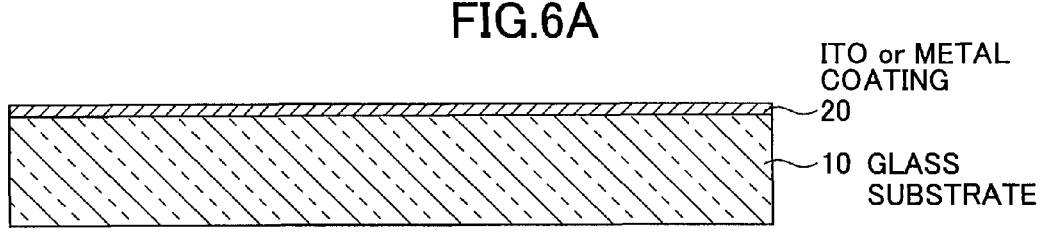
FIG. 6A is a first view showing a fabrication process of a glass substrate for imprint of the second embodiment of coating a glass substrate with a transmissive conductive film.

FIG. 6A is a view showing a state where the whole surface of the glass substrate 10 is coated with the transmissive conductive film 20. Thus, in the fabrication process of the glass substrate for imprint 30a of the second embodiment, a surface for forming the fine pattern 15 (i.e., a flat surface before processing) of the glass substrate 10 is coated with the transmissive conductive film 20 such as an ITO film.

Figure 6B:
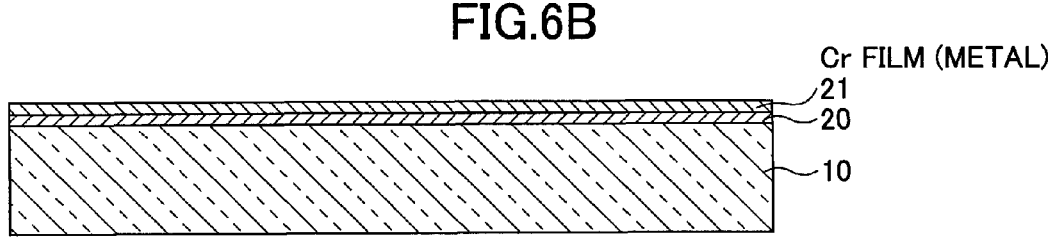
FIG. 6B is a second view showing a fabrication process of the glass substrate for imprint of coating the transmissive conductive film with a metal film.

FIG. 6B is a view showing a process coating the transmissive conductive film 20 with a metal film 21. The metal film 21 acts as a hard pattern mask. The metal film 21 may, for example, be a Cr film.

Figure 6C:
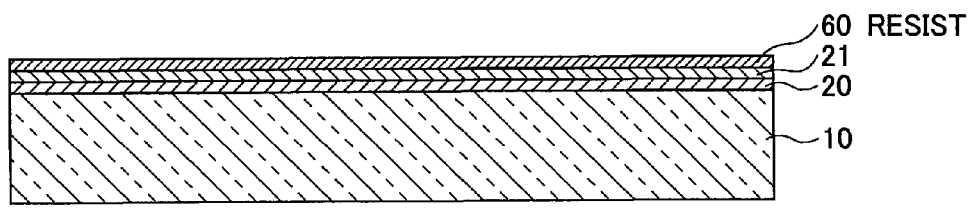
FIG. 6C is a third view showing a fabrication process of the glass substrate for imprint of the second embodiment of coating the metal film with a resist film.

FIG. 6C is a view showing a process of coating the metal film 21 with resist 60. This leads to a state capable of etching the metal film 21.

Figure 6D:
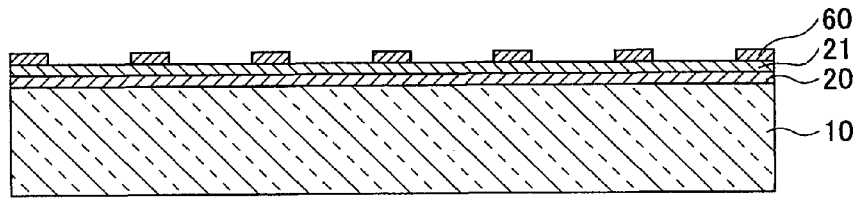
FIG. 6D is a fourth view showing a fabrication process of the glass substrate for imprint of the second embodiment of forming a resist pattern.

FIG. 6D is a view showing a process of etching the resist 60 and forming a resist pattern. A suitable method for microfabrication such as reactive ion etching is applicable to etching of the resist 60. Thus, the resist pattern is formed.

Figure 7A:
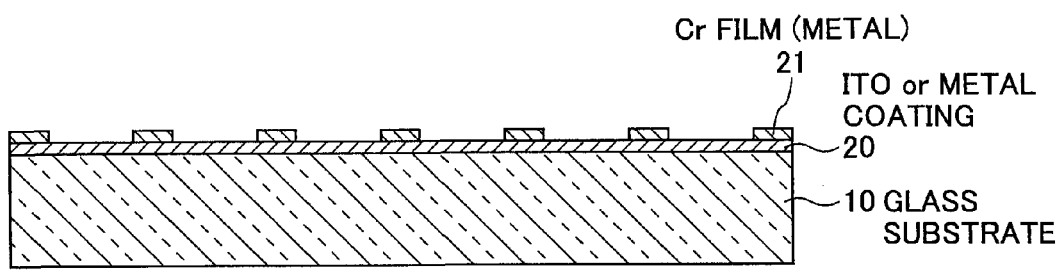
FIG. 7A is a fifth view showing a fabrication process of the glass substrate for imprint of the second embodiment of forming a pattern in the metal film.
Figure 7B:
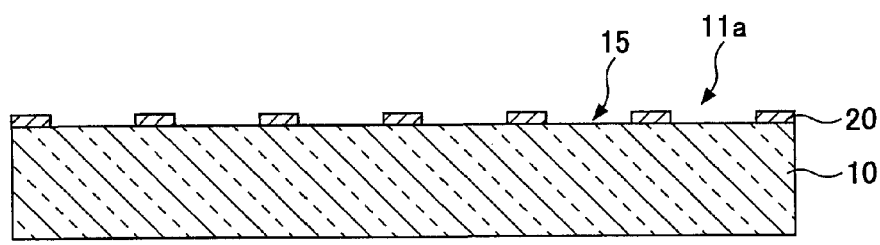
FIG. 7B is a sixth view showing a fabrication process of the glass substrate for imprint of the second embodiment of forming a fine pattern in the transmissive conductive film.
Figure 7C:
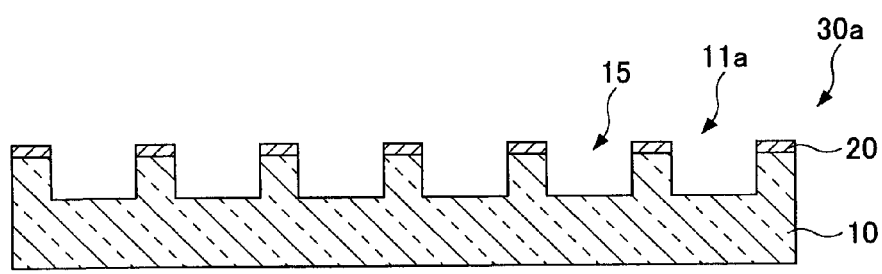
FIG. 7C is a seventh view showing a fabrication process of the glass substrate for imprint of the second embodiment of completing the glass substrate for imprint.

FIGS. 7A through 7C are views showing processes of the fabrication process of the glass substrate for imprint 30a of the second embodiment after the resist pattern formation to the completion of the glass substrate for imprint 30a.

FIG. 7A is a view showing a process of etching the metal film 21 and forming a pattern of the metal film 21 as the hard pattern mask. This makes it possible to form the fine pattern 15 on the transmissive conductive film 20 by working the metal film 21 as the mask.

FIG. 7B is a view showing a process of etching the transmissive film 20 and forming the fine pattern 15 in the transmissive film 20. As shown in FIG. 7B, the process configures a state where the transmissive conductive films 20 are left on parts which are expected to form the convex parts 12 of the fine pattern 15 on the glass substrate 10.

FIG. 7C is a view showing a process of etching the glass substrate 10 and completing the glass substrate for imprint 30a of the second embodiment. In FIG. 7C, the fine pattern 15 is formed on the glass substrate 10, and the pattern surface 11 is completed.

Then, the processes of FIGS. 7A through 7C perform all of the pattern formations by etching. As above-mentioned, the suitable method for microfabrication such as the ion reaction etching may be applicable to the etching. According to the etching, it is possible to form the fine pattern 15 with high accuracy because depth and/or angle of concave parts 13 can be controlled with high accuracy. In the fabrication process of the glass substrate for imprint 30 of the first embodiment, it is difficult to control film thickness of a side wall of the fine pattern 15 and a corner part of the concave parts 13 because the transmissive conductive film 20 is formed by vapor deposition after forming the fine pattern 15. For example, the transmissive conductive film tends to become partially thick, or the corner part tends to become rounded. However, according to the fabrication process of the glass substrate for imprint 30*a* of the second embodiment, the pattern transfer and the resist hardening without variation factor such as the rounded corner part or the thickness non-uniformity, can be realized because the transmissive conductive films 20 exist only on the convex parts 12. Furthermore, the fabrication process of the glass substrate for imprint 30*a* enables the electric potential of the convex parts 12 of the pattern surface 11*a* to be stable. In the fabrication process of the glass substrate for imprint 30*a* of the second embodiment, metal film such as Au, Pt, Al, Ta, Cr and CrN, DLC (i.e., Diamond-like Carbon), carbon and conductive organic film can substitute for the transmissive conductive film 20. Though these materials have low ultraviolet light transmittance, the glass substrate for imprint 30*a* of the second embodiment makes it possible to transmit the ultraviolet light from the uncoated side wall and bottom of the concave part 13 of the fine pattern 15 and to harden the resist 60.

Thus, according to the glass substrate for imprint 30*a*, since it is possible to form a pattern after coating the whole glass substrate 10 with the transmissive conductive film 20 without using the vapor deposition, enhancing the accuracy of a pattern formed on the glass substrate 10 and making the glass substrate for imprint 30*a* as a mask with a high-accuracy pattern are possible.

Moreover, by using the glass substrate for imprint 30*a*, it is possible to form the resist pattern with high accuracy on a substrate such as the silicon substrate 40 and to cause the electric potential of the pattern surface 11*a* to be stable. Therefore, a pattern inspection and an extraneous substance inspection of the glass substrate for imprint 30*a* by the projection-type electron beam defect detection apparatus can be realized.

FIGS. 8A through 8D are views showing a fabrication process of the glass substrate for imprint 30*a* of the second embodiment different from FIGS. 6A through 6D and FIGS. 7A through 7C.

Figure 8A:
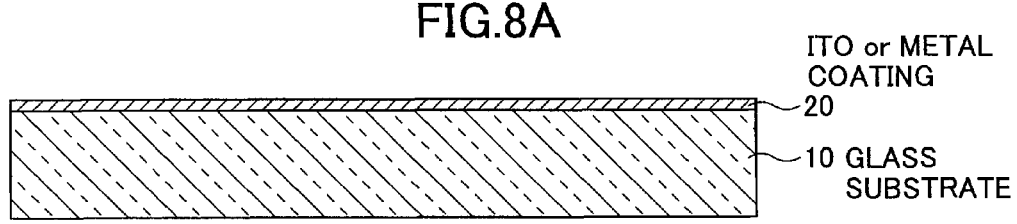
FIG. 8A is a first view showing another fabrication process of a glass substrate for imprint of the second embodiment of coating a glass substrate with a transmissive conductive film.

FIG. 8A is a view showing a process coating the whole surface of a glass substrate 10 with a transmissive conductive film 20. Since this process is similar to the process of FIG. 6A, the same referential numbers are given to constructional elements corresponding to those of FIG. 6A, and the explanation about the corresponding constructional elements is omitted.

Figure 8B:
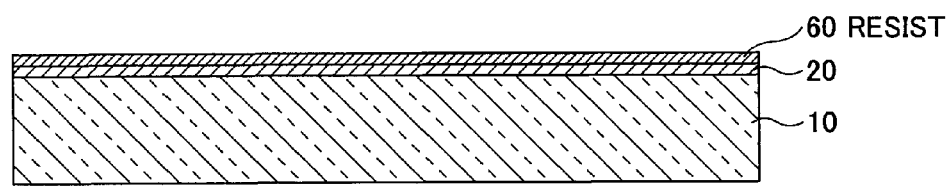
FIG. 8B is a second view showing another fabrication process of the glass substrate for imprint of the second embodiment of coating the transmissive conductive film with a resist film.

FIG. 8B is a view showing a process of coating the transmissive conductive film 20 with resist 60. Thus, without forming a metal film 21 on the transmissive conductive film 20, forming resist 60 directly on the transmissive conductive film 20 is possible.

Figure 8C:
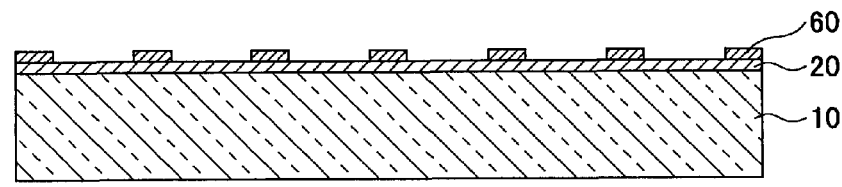
FIG. 8C is a third view showing another fabrication process of the glass substrate for imprint of the second embodiment of etching the resist film.

FIG. 8C is a view showing a process of etching the resist 60. The etching may be performed by an etching method capable of microfabrication such as the ion reaction etching.

Figure 8D:
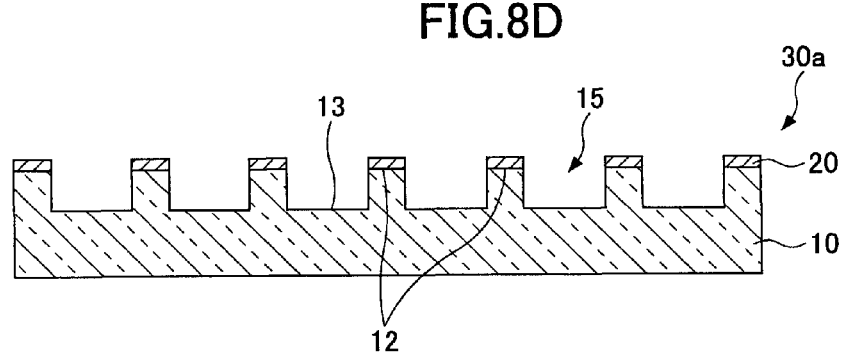
FIG. 8D is a fourth view showing another fabrication process of the glass substrate for imprint of the second embodiment of completing the glass substrate for imprint.

FIG. 8D is a view showing a process of etching the transmissive conductive film 20 and the glass substrate 10, and completing the glass substrate for imprint 30*a* of the second embodiment. In FIG. 8D, because the processing is performed by the etching, the side walls and bottoms of the concave parts 13 are sufficiently controlled, and the high-accuracy fine pattern 15 can be formed.

Thus, without forming the metal film 21, the resist film 50 can be directly formed on the transmissive conductive film 20, and the etching can be performed.

In addition, the resist pattern forming method explained in FIGS. 3A through 3D is performable using the glass substrate for imprint 30*a* of the second embodiment. According to the glass substrate for imprint 30*a*, since the fine pattern 15 of the pattern surface 11*a* can be formed with high accuracy, high-accuracy resist pattern is formed in the resist film 50 on the silicon substrate 40.

Embodiment 3

Figure 9:
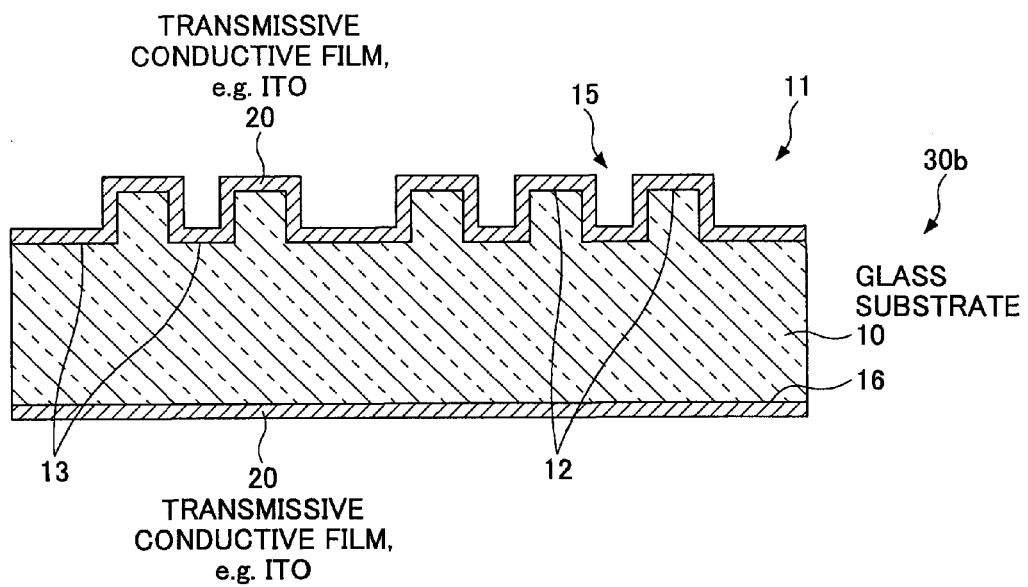
FIG. 9 is a view showing an example of a cross-sectional configuration of a glass substrate for imprint of a third embodiment of the present invention.

FIG. 9 is a view showing an example of a cross-sectional configuration of a glass substrate for imprint 30*b* of a third embodiment. In FIG. 9, the glass substrate for imprint 30*b* of the third embodiment is similar to the glass substrate for imprint 30 of the first embodiment in that the whole area of a pattern surface 11 is coated with the transmissive conductive film 20. However, the glass substrate for imprint 30*b* of the third embodiment differs from the glass substrate for imprint 30 of the first embodiment in that the back side 16 of the glass substrate 10 is also coated with the transmissive conductive film 20.

Thus, the glass substrate for imprint 30*b* of the third embodiment may be configured in a way that the back side 16 of the glass substrate 10 is also coated with the transmissive conductive film 20 as well as the pattern surface 11. This causes electric potential of the back side 16 of the glass substrate for imprint 30*b* to be stable, which allows the whole electric potential of the glass substrate for imprint 30*b* to be stable, and leads the electrical potential of the pattern surface 11 to be further stable.

In addition, a fabrication method of the glass substrate for imprint 30*b* of the third embodiment may be performed by additionally coating the back side 16 of the glass substrate 10 with the transmissive conductive film 20 by vapor deposition or plating. The glass substrate for imprint 30*b* of the third embodiment can be produced as explained in the first embodiment.

Moreover, the glass substrate for imprint 30*b* is applicable to the resist pattern forming method explained in FIG. 3 of the first embodiment. Also, as explained in FIG. 3 of the first embodiment, the resist pattern forming method with the glass substrate for imprint 30*b* is also applicable to any substrate other than the silicon substrate 40. Thus, detailed description on this point is omitted.

According to the glass substrate for imprint 30*b* of the third embodiment, the electric potential of the pattern surface can be stable, and more high-accuracy inspection can be performed in the pattern inspection by the electron beam.

Embodiment 4

Figure 10:
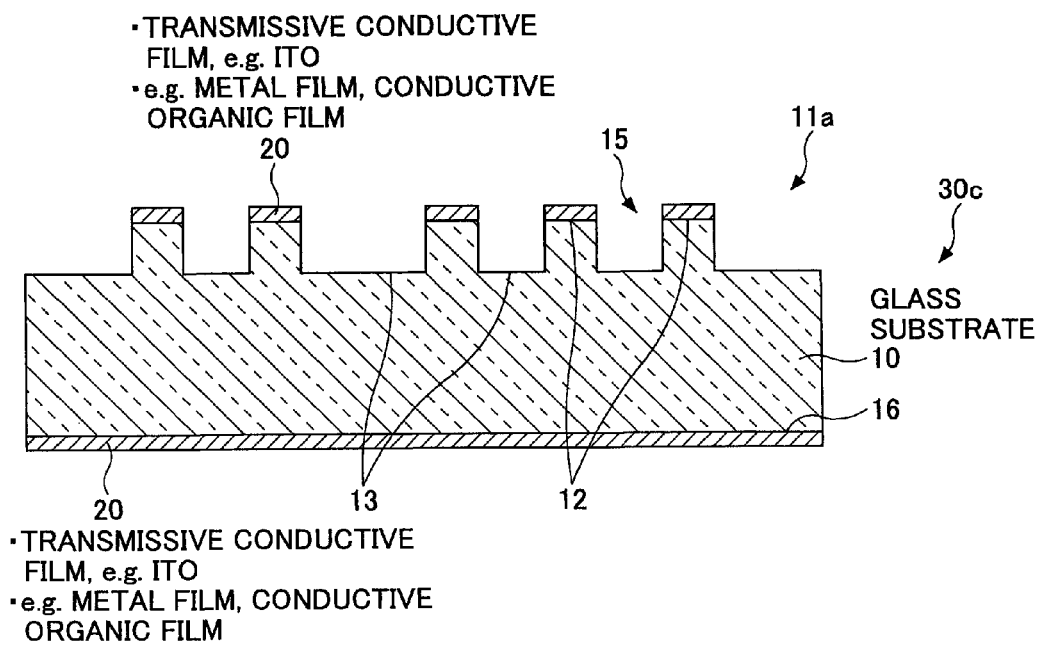
FIG. 10 is a view showing an example of a cross-sectional configuration of a glass substrate for imprint of a fourth embodiment of the present invention.

FIG. 10 is a view showing an example of a cross-sectional configuration of a glass substrate for imprint 30*c* of a fourth embodiment. In FIG. 10, the glass substrate for imprint 30*c* of the fourth embodiment is similar to the glass substrate for imprint 30*a* of the second embodiment in that only convex parts 12 of the fine pattern 15 on the pattern surface 11*a* are coated with the transmissive conductive film 20. However, the glass substrate for imprint 30*c* of the fourth embodiment differs from the glass substrate for imprint 30*a* of the second embodiment in that a back side 16 of the glass substrate 10 is also coated with the transmissive conductive film 20.

Thus, the back side 16 of the glass substrate 10 may be coated with the transmissive conductive film 20 as well as the third embodiment. This makes it possible to stabilize electric potential of the back side 16 of the glass substrate for imprint 30c and thereby to stabilize electric potential of the whole glass substrate for imprint 30c. Moreover, this makes it possible to further stabilize the electric potential of the pattern surface 11a of the glass substrate for imprint 30c, to prevent the pattern surface 11a from occurring charging and to inspect the pattern surface 11a with high accuracy. Being able to form the fine pattern 15 of the pattern surface 11a with high accuracy is similar to the second embodiment.

The glass substrate for imprint 30c of the fourth embodiment can be produced by using the almost same fabrication method of the glass substrate for imprint 30a of the second embodiment. More specifically, in FIG. 6A and FIG. 8A of the second embodiment, by preparing a glass substrate 10 whose back side is also coated with the transmissive conductive film 20 at first and then by performing the process FIGS. 6B through 7C and FIGS. 8B through 8D, the fabrication process of the glass substrate for imprint 30a is applicable to the fabrication process of the glass substrate for imprint 30c of the fourth embodiment.

In addition, regarding a resist pattern forming method, the resist pattern forming method described in FIGS. 3A through 3D can be performed by using the glass substrate for imprint 30c of the fourth embodiment. Furthermore, the resist pattern forming method with the glass substrate for imprint 30c of the third embodiment is also applicable to any substrates as well as the silicon substrate 40.

According to the glass substrate for imprint 30c, the fine pattern 15 formed on the pattern surface 11a can be formed with high accuracy, and what's more, the electro potential of the pattern surface 11a can be further stabilized, and the high-accuracy inspection by the electron beam can be performed.

Embodiment 5

A fifth embodiment of the present invention gives an explanation of an example of an inspection method and an inspection apparatus of the glass substrate for imprint 30, 30a to 30c. The inspection method and apparatus of the glass substrate for imprint 30, 30a to 30c are commonly applicable to the glass substrate for imprint 30, 30a to 30c.

Figure 11:
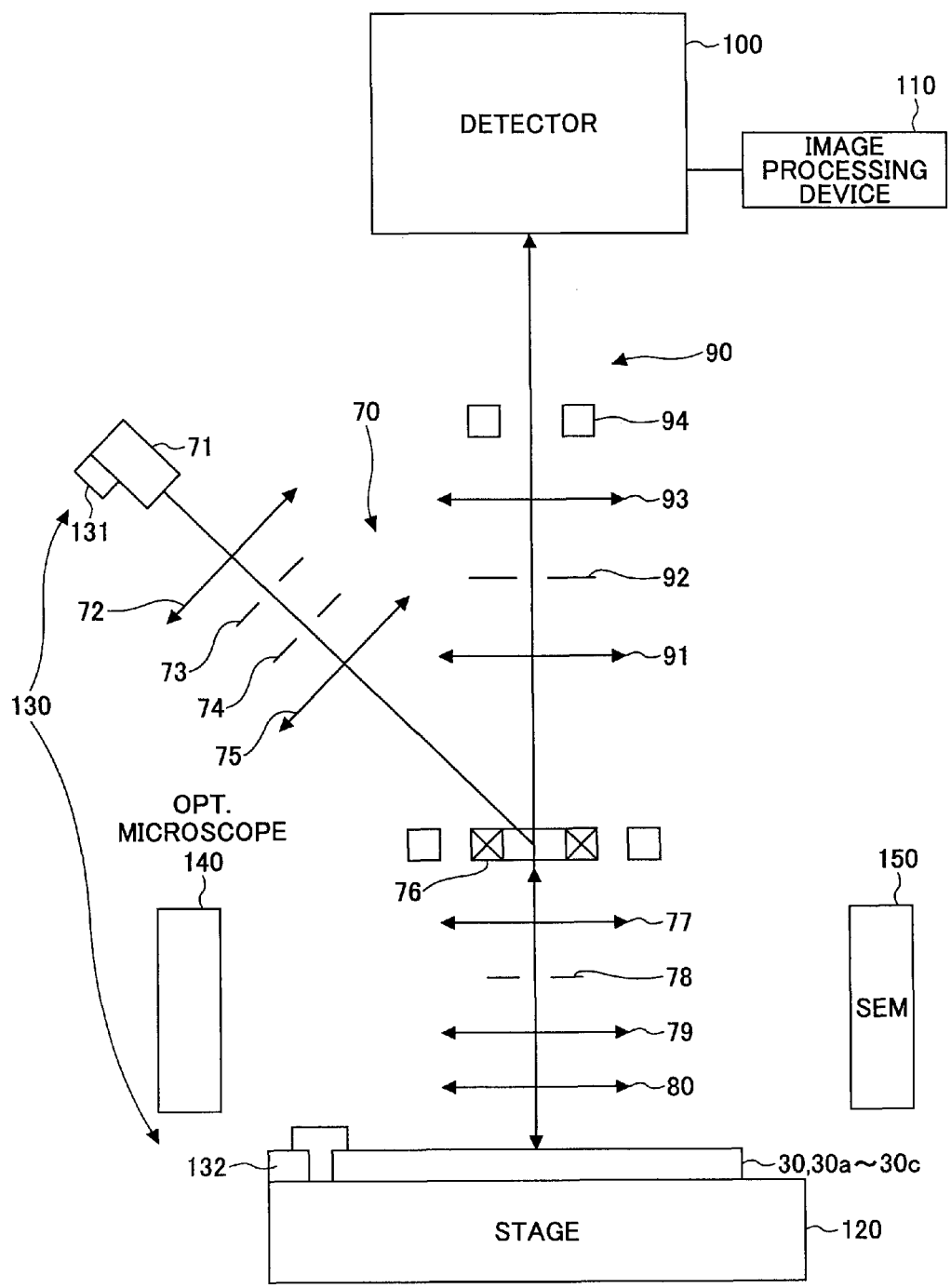
FIG. 11 is a view showing an example of an entire configuration of an inspection apparatus of a glass substrate for imprint of a fifth embodiment of the present invention.

FIG. 11 is a view showing an example of the whole configuration of the inspection apparatus of the glass substrate for imprint 30, 30a to 30c. The inspection apparatus of the glass substrate for imprint 30, 30a to 30c of the fifth embodiment constitutes a projection-type inspection apparatus.

The inspection apparatus of the glass substrate for imprint 30, 30a to 30c of the fifth embodiment includes a first optical system 70 for generating an electron beam, a stage 120 for supporting the glass substrate for imprint 30, 30a to 30c, a second optical system 90 for providing a magnified image based on emission electrons emanating from a sample or mirror electrons reflected from a sample, a detector 100 for detecting those electrons, an image processing device 110, an optical microscope 140 for alignment and a SEM (i.e., Scanning Electron Microscope) 150 for review.

The first optical system 70 is a unit that generates the electron beam and irradiates the glass substrate for imprint 30, 30a to 30c with the electron beam. The first optical system 70 includes an electron gun 71, lenses 72, 75, apertures 73, 74, an E×B filter 76, lenses 77, 79, 80 and an aperture 78. The electron gun 71 generates an electron beam. The lenses 72, 75 and apertures 73, 74 reshape and direct the electron beam. The E×B filter 76 provides the electron beam with Lorentz force by electric field and magnetic field, deflects the electron beam incident from an oblique direction in a vertical downward direction and directs the electron beam to the glass substrate for imprint 30, 30a to 30c. The lenses 77, 79, 80 direct the electron beam, slow down the electron beam properly and adjust the landing energy LE.

The electron beam with which the first optical system 70 irradiates the glass substrate for imprint 30, 30a to 30c is an electron beam having a predetermined irradiation area which corresponds to an area including a plurality of pixels on the detector 100. Therefore, the first optical system 70 can irradiate a broad area of the pattern surface 11, 11a by one-time irradiation with the electron beam. For example, the first optical system 70 may irradiate the glass substrate for imprint 30, 30a to 30c with a round electron beam of which diameter is 300 μm or an elliptic beam of about 270×80 μm.

An adjustment of landing energy LE is performed by a landing energy setting unit 130. The landing energy setting unit 130 includes an acceleration voltage set unit 131 that sets a cathode potential of the electric gun 71 and substrate voltage adjustment mechanism 132 that sets substrate potential on the stage 120. The landing energy setting unit 130 sets and adjusts a desired landing energy LE by adjusting electric potential difference between the electron gun 71 and the stage 120, using the acceleration set unit 131 and the substrate voltage adjustment mechanism 132.

The first optical system 70 may irradiate the glass substrate for imprint 30, 30a to 30c with both a first electron beam for pre-charge and a second electron beam for imaging.

The stage 120 is a unit that supports the disposed glass substrate for imprint 30, 30a to 30c and is movable in a horizontal direction of x-y plane and θ direction. In addition, the stage 120 may be movable in z direction (i.e., vertical direction), if needed or desired. The stage 120 may include a sample fixation mechanism such as an electrostatic chuck on its surface.

The substrate voltage adjustment mechanism 132 is provided with the stage 120. The substrate voltage adjustment mechanism 132 adjusts the landing energy LE of the electron beam by adjusting the electric potential of the glass substrate for imprint 30, 30a to 30c. Negative voltage is applied to the glass substrate for imprint 30, 30a to 30c. An electric potential of a principal surface of the first lens 80 of the second optical system 90 is positive. Therefore, positive electric field is formed in the vicinity above the glass substrate for imprint 30, 30a to 30c. For example, the substrate voltage may be set in a range of 1 to 3 kV/mm.

The glass substrate for imprint 30, 30a to 30c is disposed on the stage 120 and the first optical system 70 irradiates the pattern surface 11, 11a with the electron beam of which landing energy LE is −5 to −10 eV. If there is an extraneous substance 250 on the pattern surface 11, 11a, of the glass substrate for imprint 30, 30a to 30c, the extraneous substance 250 becomes charged. Because of this, incident electrons from the first optical system 70 are reflected without contacting the extraneous substance 250 on the glass substrate for imprint 30, 30a to 30c and mirror electrons are led to the detector 100 by the second optical system 90. On the other hand, regarding a normal part without the extraneous substance 250, secondary emission electrons (which include secondary electrons, reflection electrons, back scattered electrons and a combination of the electrons) are led to the detector 100 by the second optical system 90. Then, because the secondary emission electrons emanate from the sample surface in a widespread direction, a transmittance becomes a low value, for example, a degree of 0.5 to 4.0 percent. In contrast, since the mirror electrons do not spread out, a high transmittance of nearly 100 percent can be attained. Therefore, only signals corresponding to the extraneous substance 250 forming the mirror electrons are detected with high luminance (which means a state including many electrons), having a high difference from the surrounding secondary emission electrons. This makes it possible to achieve high contrast.

Furthermore, an image by the mirror electrons is naturally magnified larger than optical magnification. FIGS. 12A through 12C are views showing an extraneous substance image on the pattern surface 11 obtained by the inspection method of the glass substrate for imprint 30, 30a to 30c and a principle outline.

FIG. 12A is a view showing an image 280 of the extraneous substance 250 of a size of 40 nm obtained by the inspection method and apparatus of the glass substrate for imprint 30, 30a to 30c. In FIG. 12A, the extraneous substance 250 is a size that almost fills an area of pixel size of 2×2 µm. The pixel size means an actual size on a sample corresponding to a pixel of a detector and means a minimum unit size capable of being seen on the sample. Accordingly, in FIG. 12A, though actual size of the extraneous substance 250 is 40 nm, the extraneous substance 250 is displayed by being magnified to a degree of approximately 2×2 µm in the image 280. This means, for example, even if the sample surface is inspected in a degree of pixel size of 1 µm, 1.5 µm, the extraneous substance 250 of a degree of 40 nm can be discovered. In FIG. 12A, the landing energy LE of the electron beam for imaging is 1 eV and the pixel size is 100 nm. Usually, if the actual size of the extraneous substance 250 is 40 nm, the pixel size less than 40 nm is required to image the extraneous substance 250. However, in the inspection method of the embodiment, it is possible to obtain the magnified image of the extraneous substance 250 magnified more largely than the optical magnification.

FIG. 12B is a view showing an image 281 of the extraneous substance 250 having the size of 40 nm obtained by the conventional inspection method of SEM (i.e., Scanning Electron Microscope) type. In FIG. 12B, the image of the extraneous substance 250 in the pixel size of 2×2 nm same as FIG. 12A is shown. The image 281 displays the extraneous substance 250 in a much smaller size than that of the image 280 shown in FIG. 12A.

Thus, the electron beam inspection method of the embodiment can obtain the image by considerably magnifying the size of the extraneous substance 250 compared to the conventional SEM type inspection method. More specifically, the electron beam inspection method makes it possible to detect a signal from the extraneous substance 250 by magnifying larger than the optical magnification. Furthermore, it is possible not only to realize a high sensitivity to the extraneous substance 250 of the ultra-micro size but also to detect the extraneous substance 250 using the larger pixel size than the actual size of the extraneous substance 250.

FIG. 12C is a lateral view showing a state where the extraneous substance 250 is on the pattern surface 11, 11a of the glass substrate for imprint 30, 30a to 30c. In FIG. 12C, the fine pattern 15 is omitted for easy understanding. The state may be considered to be a state where the extraneous substance 250 is on the convex part 12. In FIG. 12C, since a surface of the extraneous substance 250 is a spherical surface, an electronic signal reflected from the surface travels by changing the path in a diverging way, not vertically. This is because the extraneous substance 250 has a sphere surface figure, whose electric potential distribution differs from the pattern surface 11, 11a, and the electric potential distribution of the part where the extraneous substance 250 exists is distorted when the pattern surface 11, 11a is observed in a broad perspective.

Figure 13A:
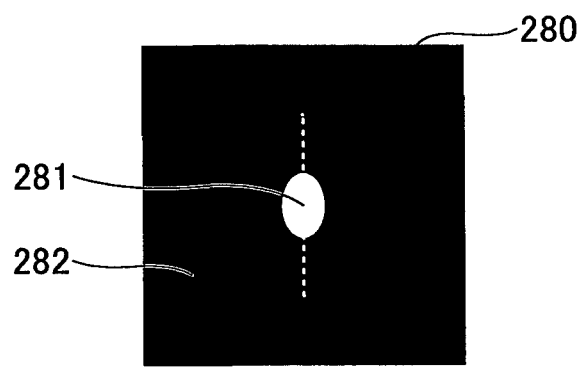
FIG. 13A is a view showing an example of a magnified image of the extraneous substance.
Figure 13B:
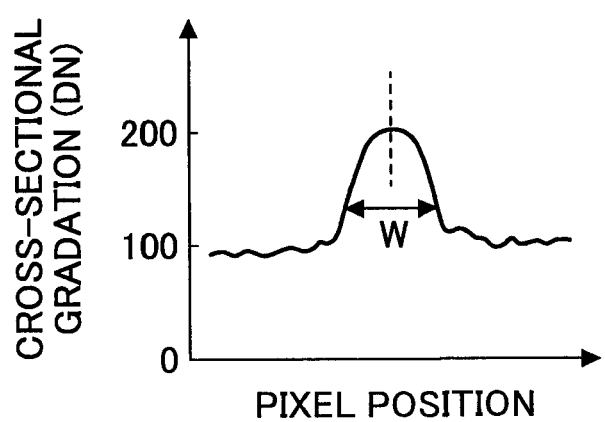
FIG. 13B is a view showing an example of cross-sectional gradation of the magnified image of the extraneous substance in pixel positions.

FIG. 13A and FIG. 13B are views showing an example of a magnified image 280 of the extraneous substance 250 obtained by an extraneous substance inspection method of the present invention and a cross-sectional gradation. FIG. 13A is a view showing the magnified image 280 of the extraneous substance 250 obtained by the extraneous substance inspection method. In FIG. 13A, a central white area shows a magnified image 281 of the extraneous substance 250, and a black area shows a surface image 282 of the pattern surface 11, 11a of the glass substrate for imprint 30, 30a to 30c. In FIG. 13A, the extraneous substance size (which means diameter) is 40 nm and the optical magnification is 300 times. In this case, according to a conventional extraneous substance inspection method, an image of the extraneous substance 250 is 40 nm×optical magnification 300=12 µm. However, according to the extraneous substance inspection method of the present invention in FIG. 13A, the size of the extraneous substance 250 in the magnified image 281 is 190 nm. Also, pixel size of the detector 100 is 15 nm.

FIG. 13B is a view showing a cross-sectional gradation at a pixel position. The horizontal axis shows pixel position coordinate and the vertical axis shows the cross-sectional gradation. In FIG. 13B, the part having a peak W is an area where the gradation is high, and the part corresponds to the magnified image 281, the white area in FIG. 13B. More specifically, the width W of the magnified image 281 in the image 280 is 190 µm. Then, since the pixel size of the detector 100 is 15 µm, according to a conventional method, the extraneous substance size is displayed as 12 µm in the image 280. Hence, the image of the extraneous substance 250 becomes a signal less than 1 pixel and the extraneous substance 250 cannot be accurately displayed at one pixel.

In contrast, according to the inspection method and apparatus of the glass substrate for imprint 30, 30a to 30c of the embodiment, the magnified image 281 of the extraneous substance 250 can be detected at 12.7 pixel size. Hence, it is possible to image the extraneous substance 250 at a larger pixel size with less magnification ratio. When imaging at a large pixel size is possible, inspecting the whole pattern surface 11, 11a with high speed becomes possible, which makes an extraneous substance inspection with high speed and high throughput possible. For example, when the extraneous substance size is 10 to 30 nm, the pixel size of 100 to 1000 nm larger than the extraneous substance size is used, which makes a high-speed inspection possible.

Thus, an image from mirror electrons is magnified larger than the optical magnification, and the actual magnification ratio reaches 5 to 50 times. Under typical conditions, it is often the case that the magnification ratio becomes 20 to 30 times. Then, detection at a pixel size more than three times larger than the extraneous substance 250 is possible, which realizes the high-speed and high-throughput extraneous substance inspection. Hence, for example, regarding the extraneous substance 250 with the size of 20 nm in diameter, the imaging and inspection using the pixel size more than three times larger than the extraneous substance size are possible. Specifically, for example, 60 nm pixel size, 100 nm pixel size and 500 nm pixel size are available. This is a prominent advantageous feature for the high throughput, compared to the SEM type inspection.

The explanation returns to FIG. 11. The second optical system 90 is a unit that leads reflected and/or emitted electrons from the glass substrate for imprint 30, 30a to 30c to the detector 100. The second optical system 90 includes lenses 91, 93, an NA aperture 92 and an aligner 94. The reflected and/or emitted electrons from the pattern surface 11, 11a of the glass substrate for imprint 30, 30a to 30c pass through an objective lens 80, the lens 79, the aperture 78, the lens 77 and the E×B filter 76 again and are lead to the second optical system 90. Then, the reflected and/or emitted electrons from the pattern surface 11, 11a is imaged on the detector 100 by the projection optical system at the magnification ratio of 50 to 500 times. In the second optical system 90, the electrons are collected through the lens 91, NA aperture 92 and lens 93, adjusted by the aligner 94 and detected by the detector 100.

Figure 14B:
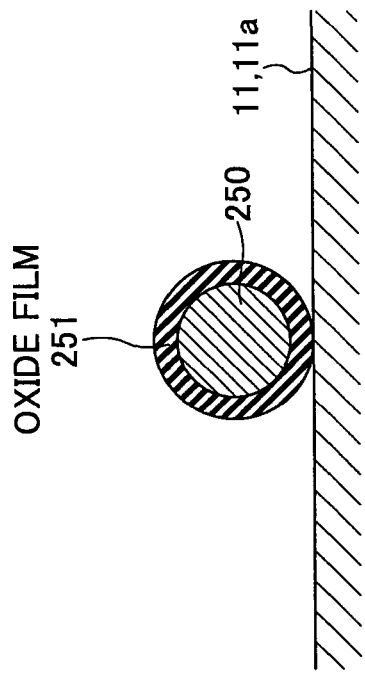
FIG. 14B is a magnified cross-sectional view showing the extraneous substance.
Figure 14A:
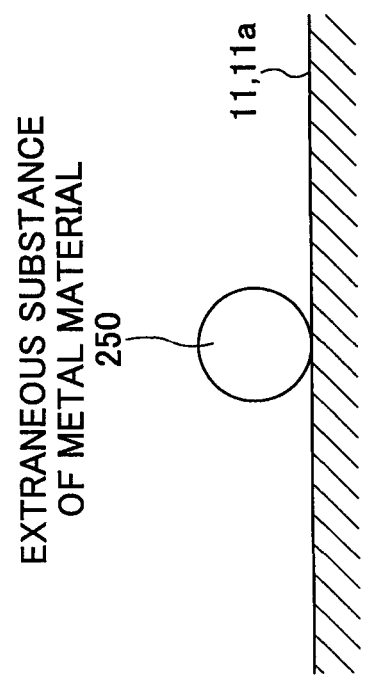
FIG. 14A is a lateral view showing the extraneous substance of metal materials.

The extraneous substance 250 includes materials such as a semiconductor, an insulator and a metal. FIG. 14A and FIG. 14B are views showing the extraneous substance 250 of a metal material. FIG. 14B is a magnified cross-sectional view showing the extraneous substance 250 of the metal material. In FIG. 14B, even if the extraneous substance 250 includes metal, insulator or mixture of them, a natural oxide film 251 is formed on a surface of the extraneous substance 250, which is covered with insulating material. Thus, regarding the extraneous substance 250 of metal material, charging by the natural oxide film 251 occurs and may be utilized for imaging.

The explanation returns to FIG. 11. The detector 100 is a unit that detects electrons led by the second optical system 90. The detector 100 includes a plurality of pixels on its detection surface. Because of the plurality of pixels on the detection surface, the detector 100 can detect a plurality of electrons generated by irradiation of the electron beam with a predetermined area simultaneously and two-dimensionally. A variety of two-dimensional detectors are available for the detector 100. For example, a CCD (i.e., Charge Coupled Device) sensor or a TDI (i.e., Time Delay Integration)-CCD sensor is applicable to the detector 100. If the TDI-CCD sensor is applied to the detector 100, the detector 100 includes a MCP (i.e., Micro Channel Plate), a fluorescent screen, a relay lens and the TDI-CCD sensor. The MCP multiplies quantity of detected electrons and the florescent screen converts the electrons into light signals. These two-dimensional light signals are imaged on the TDI-CCD sensor and detected. Because the TDI-CCD sensor can detect a two-dimensional image while a sample is moving continuously, high-speed image signal obtaining is possible. The image processing device 110 performs electron image formation, defect detection and defect classification based on the signals from the TDI-CCD sensor. However, since the CCD sensor and TDI-CCD sensor are sensors that detect the signal after converting the electrons into light, a unit for photoelectric conversion is necessary. Hence, as mentioned above, the conversion process converting the electrons into the light with the fluorescent screen or a scintillator, and transmitting light image information to the TDI-CCD sensor that detects the light is needed.

Considering the conditions, in the fifth embodiment, an explanation is given by showing an example where an EB (i.e., Electron Beam)-TDI sensor is applied to the detector 100. The EB-TDI sensor does not need the photoelectric conversion mechanism and the light transmission mechanism. The EB-TDI sensor directly receives the electrons on a sensing surface of its own. This prevents deterioration of resolution and makes it possible to obtain high MTF (i.e., Modulation Transfer Function) and contrast. With the EB-TDI sensor, it is possible to enhance S/N (i.e., signal to noise) of a weak signal of the small extraneous substance 250 unstable to detect and to obtain higher sensitivity. The enhancement of the S/N reaches 1.2 to 2 times.

In addition, by providing an EB-CCD sensor adding to the EB-TDI sensor, using both the EB-TDI sensor and EB-CCD sensor in an interchangeable way at will is effective. For example, usage shown in FIG. 15 is possible.

Figure 15:
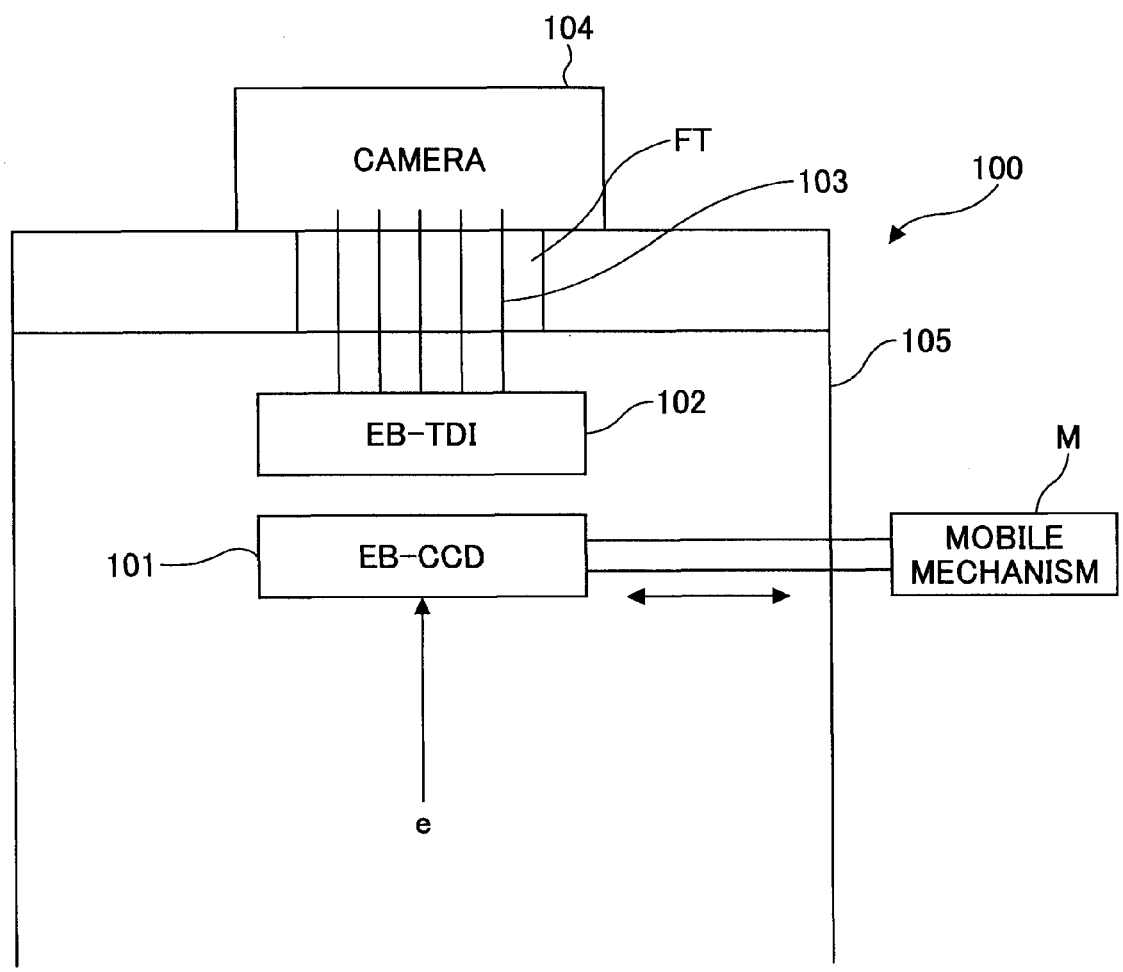
FIG. 15 is a view showing a detector capable of using both an EB-TDI sensor and an EB-CCD sensor by exchange.

FIG. 15 is a view showing a detector 100 capable of using both an EB-TDI sensor 102 and EB-CCD sensor 101 in an interchangeable way based on intended purpose. In FIG. 15, the detector 100 includes the EB-CCD sensor 101 and the EB-TDI sensor 102. The EB-CCD sensor 101 and the EB-TDI sensor 102 are electric sensors that receive the electron beam e and allow the electron beam e to directly enter their detection surfaces. In this configuration, the EB-CCD sensor 101 is used for optical axis adjustment of the electron beam e, and adjustment and optimization of imaging conditions. On the other hand, in case of using the EB-TDI sensor 102, a mobile mechanism M moves the EB-CCD 101 to a site distant from the optical axis. After that, imaging by the EB-TDI sensor 102 is performed using or referring the optical conditions obtained during the use of the EB-CCD sensor 101, and thereby the estimation or the measurement is carried out.

In the detector 100, the defect detection of the glass substrate for imprint 30, 30a to 30c by the EB-TDI 102 can be conducted by using or referring the electric optical conditions obtained when using the EB-CCD sensor 101. After the defect inspection by EB-TDI 102, it is possible to perform review imaging with the EB-CCD 101 and to carry out defect estimation about the defect types or size. At this time, the EB-CCD sensor 101 can accumulate images, which makes it possible to reduce the noise and to perform the review of imaging of the defect detection site with high S/N. Moreover, making the pixel of the EB-CCD sensor 101 smaller than that of the EB-TDI sensor 102 is effective. More specifically, this makes it possible to take an image with more pixels to the signal size magnified by the projection optical system, which leads to imaging for inspection, classification and determination of defect types with high resolution.

Moreover, the EB-TDI sensor 102 has a detection surface such as rectangular geometry on which the pixels are two-dimensionally arranged, so that the detection surface can directly receive the electron beam e and form the electron image. For example, the pixel size is 12 to 16 μm. On the other hand, the pixel size of the EB-CCD sensor 101 is, for example, 6 to 8 μm.

In addition, the EB-TDI sensor 102 is formed as a configuration of package 105. The package 105 itself plays a role of the feed through, and pins 103 of the package 105 are connected to the camera 104 on the air side.

Thus, the EB-CCD sensor 101 and EB-TDI sensor 102 can directly detect the electrons without converting the electrons to light, which allows obtaining the image of the pattern surface to be simple and easy.

The explanation goes back to FIG. 11. The image processing device 110 is a defect detection unit that generates a surface image of the pattern surface 11, 11a of the glass substrate for imprint 30, 30a to 30c from electrons detected by the detector 100 and detects a defect. Since the image processing device 110 performs arithmetic processing for image formation and defect detection, an arithmetic processing unit such as a computer may be applied.

Next, with FIG. 16A and FIG. 16B, an example of an arithmetic processing for defect detection performed by the image processing device 110 is explained. FIG. 16A and FIG. 16B are views showing an example of defect detection by die to die.

FIG. 16A is a view showing that there are a plurality of areas on which the fine pattern 15 is formed (i.e., dies) on the glass substrate for imprint 30, 30a to 30c. In FIG. 16A, a first die and a second die are shown and each die usually includes the same pattern. In this case, by comparing the same part of two dies, it is determined that the part has a defect when each of the pattern signals differs each other. In FIG. 16A, the same pattern is formed on the first die and the second die. By comparing the same pattern area of the two dies, if there is a defect either in the first die or the second die, based on a comparison image (which is obtained from differential signal by comparison), the signal of the defect part is detected and defect determination can be made.

FIG. 16B is a view showing an example of die pattern and an example of pattern defect parts. In the pattern example shown in FIG. 16B, the leftmost pattern includes a deficit, and the middle pattern includes an extra pattern. In FIG. 16B, the rightmost pattern has a normal pattern. If the die is compared to a die including all normal patterns and thereby the difference signal is obtained, the difference signal in the part of the deficit pattern and the extra pattern does not become zero. Then, a plus or minus signal is detected, and a defect part signal is detected. Thus, for example, the defect may be detected by comparing the signals between dies formed on the glass substrate for imprint 30, 30a to 30c. The defect may include the pattern defect and/or the extraneous substance attachment.

Also, without comparing two dies, comparing a die with CAD data is possible. Since the CAD data does not include the defect, by comparing the inspection image obtained from the electron beam irradiation with the CAD data, it is determined that there is a defect in the inspection image part when there is a difference.

Figure 17:
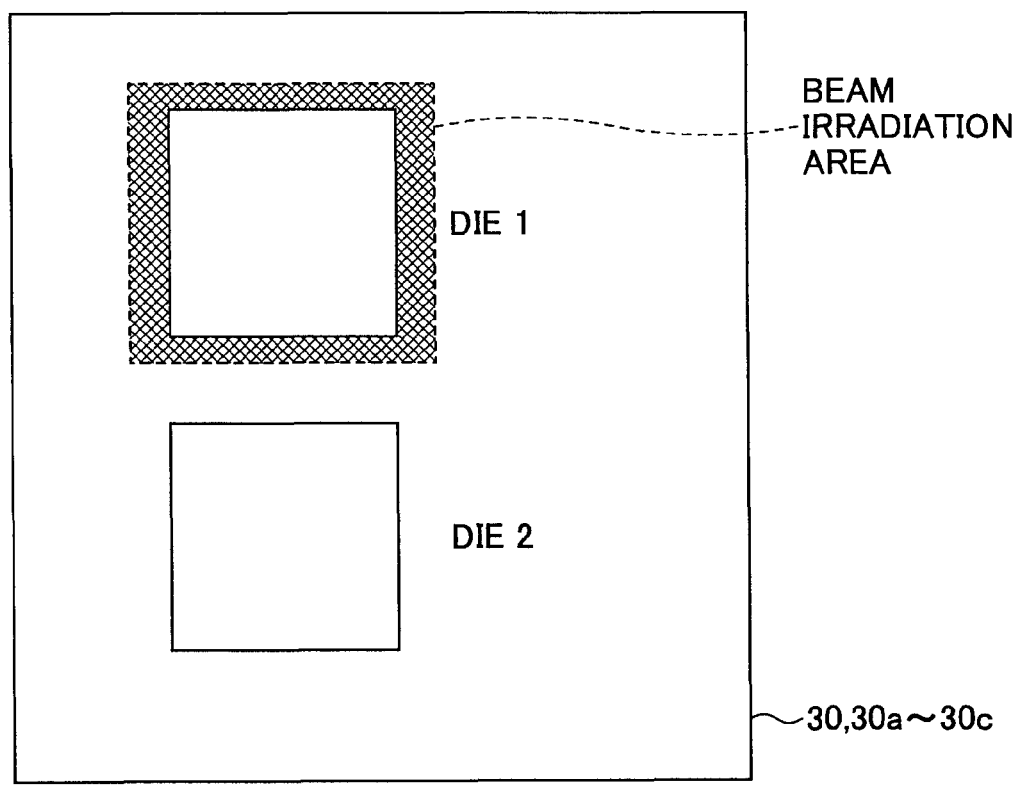
FIG. 17 is a view for explaining an example of an electron beam irradiation method.

FIG. 17 is a view for explaining an example of an electron beam irradiation method. As shown in the first die in FIG. 17, when the inspection of the die to die or the die to CAD data is performed in the pattern defect inspection, irradiating an area including a range of 5 to 500 [μm] outside with the electron beam is very effective if a particle inspection (which means the extraneous inspection) is subsequently performed as the second inspection. When the electron beam irradiation in the pattern defect inspection includes the pre-charge effect in the next particle inspection, if an area for the particle inspection (i.e., care area) is the pattern formation area in the die, the electron beam irradiation is very effective in the particle inspection. As mentioned above, irradiating outside the die with the electron beam in the first inspection causes pre-charge to the part outside of the die and enhances uniformity of the electric potential state of the surface where the pre-charge is made.

In addition, as another advantage, the following advantage is noted. When the beam is scanning, it is important to carry out the beam irradiation by unlocking the electron beam blanking outside the care area. If the beam blanking is unlocked in the care area, non-uniformity of the electron beam irradiation (i.e., dose non-uniformity) occurs in the beam blanking unlocking. Thus, to prevent such dose non-uniformity and to obtain a stable image of the care area, as shown in FIG. 17, by unlocking the electron beam blanking and starting the electron beam irradiation at a certain distance outside, the uniform image can be obtained and the high-accuracy pattern inspection becomes possible.

Next, in the inspection apparatus for imprint 30, 30a to 30c of the fifth embodiment, an explanation is given about the case where an electron beam irradiation process includes two processes of a first beam irradiation process and a second beam irradiation process, and landing energy of the first electron beam differs from that of the second electron beam.

For example, the landing energy of the electron beam in the pattern defect inspection is made as a first landing energy LE1. After that, the extraneous substance inspection in the die area is performed. Landing energy in the extraneous substance inspection is made as a second landing energy LE2. In this case, making LE1>LE2 is very effective because in the detection of the extraneous substance 250, the pre-charge by the first electron beam enables the surface electric potential of the extraneous substance 250 to be stable, which enhances detection sensitivity. By emitting the electron beam with the second landing energy less than the first landing energy causing charging to the glass substrate for imprint 30, 30a to 30c, the secondary emission electrons from the extraneous substance 250 are influenced by the charging voltage, and change their paths widely, which makes it possible to obtain the high S/N.

In addition, it is preferable for the difference between the landing energy LE1 of the first electron beam working for pre-charge and the landing energy LE2 of the second electron beam to be a degree of 5 to 20 eV, according to an experiment. Also, a range of 10 to 15 eV is further preferable. When there is an electric potential difference between the extraneous substance 250 and the surrounding, if the glass substrate for imprint 30, 30a to 30c is irradiated with the electron beam of the first landing energy LE1 in a negative charging range, the charging voltage varies depending on the first landing energy LE1 value. Based on the ratio of the first landing energy LE1 to the second landing energy LE2, when the first landing energy is large, the charging voltage is high and a reflection point is formed above the extraneous substance 250 (i.e., the detector 100 side). The position of the reflection point changes the path of the mirror electrons and the transmittance and decides the optimal charging voltage conditions. Also, if the first landing energy LE1 is too low, efficiency of the mirror electron formation decreases. In the present invention, it has been discovered and invented that the difference between the first landing energy LE1 and the second landing energy LE2 is in a range of the above mentioned range. Moreover, it is preferable for the value of the first landing energy LE1 to be 0 to 40 eV, further preferable to be 5 to 20 eV.

Thus, by using a low landing energy electron beam as the second electron beam, a pattern surface image by the mirror electrons can be obtained, whereby a high-accuracy inspection can be performed with the appropriate pattern surface image. In addition, the pattern surface image can be obtained by magnifying a defect on the pattern surface more than the optical magnification, which makes the defect detection easy.

Next, a description is given about an example where the inspection of the extraneous substance 250 on the pattern surface 11, 11a of the glass substrate for imprint 30, 30a to 30c by using the inspection apparatus of the glass substrate for imprint 30, 30a to 30c. An example where the landing energy LE of the electron beam emitted to a sample is 3 eV is given. In this case, the landing energy LE of the electron beam emitted to the sample is the difference between cathode voltage of the electron gun 71 in the first optical system 70 and the voltage (i.e., applied voltage) of the glass substrate for imprint 30, 30a to 30c. Due to this beam irradiation, the extraneous substance 250 becomes charged, and only the electron beam emitted to the extraneous substance 250 becomes the mirror electrons, which are led to the detector 100 by the second optical system 90. In a normal part without the extraneous substance 250, secondary emission electrons (which include secondary electrons, reflection electrons, backscattered electrons and combinations thereof) by the electron beam irradiation are led to the detector 100 by the second optical system 90. Then, emission rate η of the secondary emission electrons decrease (i.e., becomes closer to zero) as the landing energy LE is close to zero. Furthermore, because emission direction of the secondary electrons from the pattern surface 11, 11a has divergent distribution (for example, secondary electrons follow cosine rule), a percentage of the secondary electrons reaching the detector 100 through the second optical system 100 is in a range of a few or several percent, according to design calculation. Thus, since arrival factor of the mirror electrons is high, and arrival factor and emission rate of the surroundings are low, a relatively large range of electron number ratio, luminance difference, occurs. Accordingly, obtaining large range of contrast and S/N becomes possible. For example, under the condition of 100 nmPx and 20 nm of the extraneous substance 250, obtaining S/N=5 to 10 is possible. Usually, since S/N≥3 is sufficient for detection and inspection, it is possible to inspect such a minute extraneous substance 250 by larger pixel size than the extraneous substance size.

Next, in the inspection apparatus of the glass substrate for imprint 30, 30a to 30c of the fifth embodiment, an example of using pre-charge is described. With the landing energy LE1 for the pre-charge and the landing energy LE2 for the imaging and inspection, the extraneous substance 250 of insulator can be inspected efficiently. It is possible to inspect a transmissive conductive film 20 coating the pattern surface 11, 11a and the extraneous substance 250 on a metal film 21. In this process, the whole inspection area is irradiated with the electron beam at the first landing energy LE1. Next, by irradiating the whole inspection area with the electron beam at the second landing energy LE2, the imaging and inspection of the extraneous substance 250 can be conducted. This imaging and inspection depends on how long the pre-charge effect continues, but ordinarily, if electricity removal treatment is not conducted, it is possible to maintain the charge effect in a range of 10 to 30 hours, or more than 150 hours under good conditions.

In addition, the second landing energy LE2 of the second electron beam is preferable in a range of −10 to 10 ev, and more preferable in a range of −5 to 5 eV.

By carrying out such pre-charge, it is possible to cause an effect of the mirror electron formation to be wider and to enhance S/N by a degree of 3 to 10 times than the case without the pre-charge.

Thus, according to the proper landing energy setting, by emitting the first electron beam with a landing energy proper for adjusting the surface charging state of the glass substrate for imprint 30, 30a to 30c, and then by emitting the second electron beam with a landing energy proper for inspecting the surface of the glass substrate for imprint 30, 30a to 30c, an appropriate image can be obtained and a high-accuracy inspection can be realized. Moreover, according to the inspection method and apparatus of the embodiment 5, it is possible to irradiate the pattern surface of the glass substrate for imprint 30, 30a to 30c in a state where the pattern surface has a stable electric potential due to the transmissive conductive film 20. Also, since the two-dimensional image of the pattern surface is imaged on the detection surface by projection method using an electron beam with a broad irradiation area, the proper defect inspection of the pattern surface can be carried out with high speed and high throughput.

Embodiment 6

Figure 18:
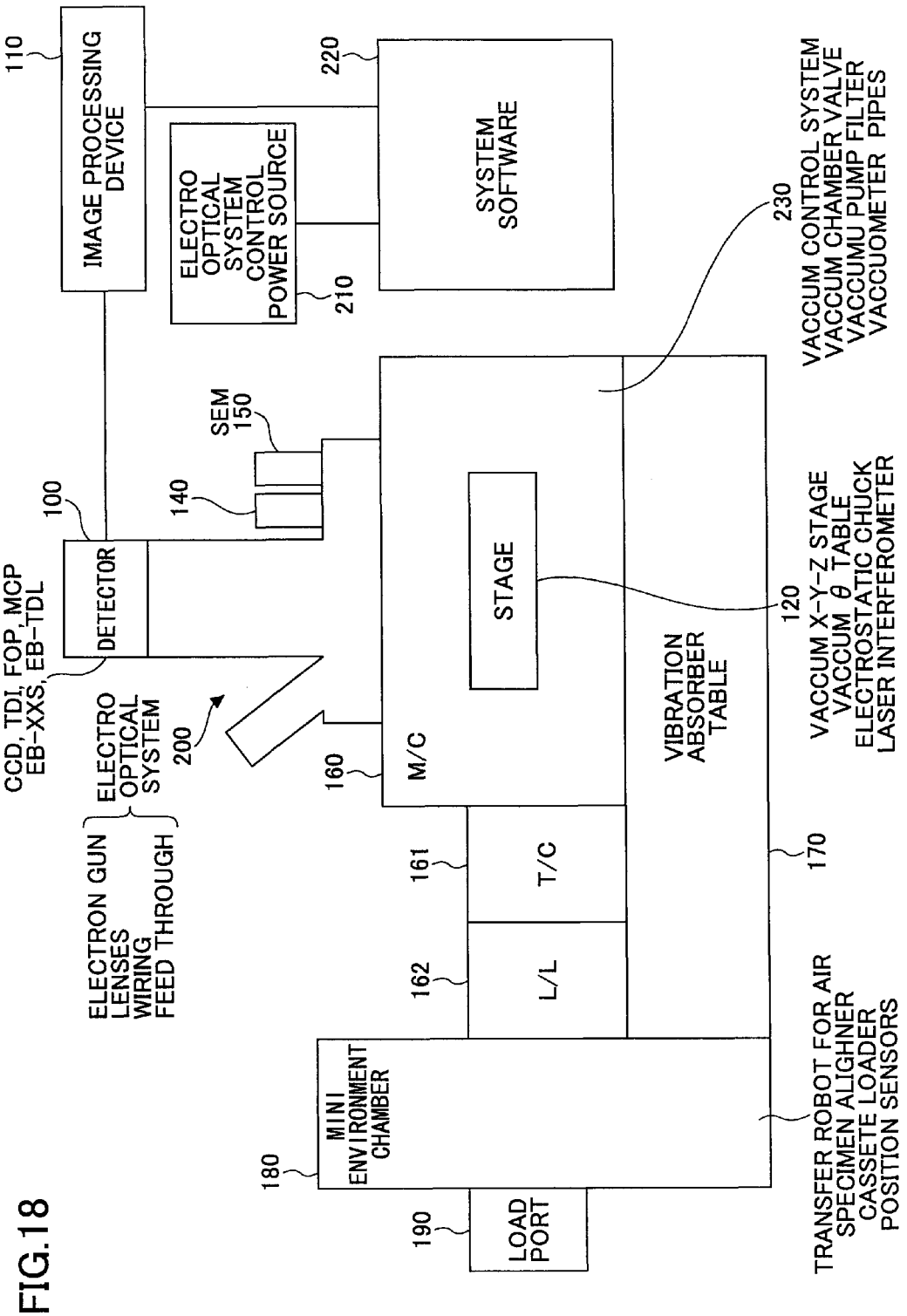
FIG. 18 is a view showing an example of a whole configuration of an inspection apparatus of a sixth embodiment of the present invention.

FIG. 18 is a view showing an example of the whole configuration of an inspection apparatus of the glass substrate for imprint 30, 30a to 30c of a sixth embodiment. In the sixth embodiment, an example of an inspection apparatus of the glass substrate for imprint 30, 30a to 30c is explained.

In FIG. 18, the inspection apparatus of the embodiment includes a load port 190, a mini environment chamber 180, a load lock chamber 162, a transfer chamber 161, a main chamber 160, an electron optical system column 200 and an image processing device system 110. The mini environment chamber 180 includes a transfer robot for air, a substrate alignment device, a clean air supply mechanism and so on (which are not shown in FIG. 18). The transfer chamber 161 includes a transfer robot for vacuum (which is not shown in FIG. 18). Since the transfer robot for vacuum is always in the vacuum transfer chamber 161, it is possible to prevent particle generation due to pressure change as little as possible.

The main chamber 160 includes a stage 120 movable in x, y, and θ (rotation) directions on which an electrostatic chuck is provided. The glass substrate for imprint 30, 30a to 30c itself, or a pallet or a jig holding the glass substrate for imprint 30, 30a to 30c is set on the electrostatic chuck.

The main chamber 160 is controlled to maintain the inside vacuum by a vacuum control system 230. In addition, the main chamber 160, transfer chamber 161 and load lock chamber 162 are disposed on a vibration absorber table 170 that prevents vibration from the floor from transmitting.

Moreover, the electron optical system column 200 is provided with the main chamber 160. This electron optical system column 200 includes columns of the first optical system 70 and the second optical system 90 and the detector 100 to detect the secondary emission electrons or the mirror electrons from the glass substrate for imprint 30, 30a to 30c. A signal from the detector 100 is transmitted to the image processing device 110 and processed. The signal processing by the image processing device 110 may be conducted during the inspection in parallel. Moreover, only the image is obtained during the inspection, and the signal processing may be also performed after the inspection individually. Data processed by the image processing device 110 is stored in a memory medium such as a hard disk and a memory. In addition, the data can be displayed in a monitor in a console, if necessary or desired. For example, an inspection area, an extraneous substance number map, an extraneous substance size distribution/map, an extraneous classification and a patch image can be displayed in the monitor. To do such a signal processing, system software 220 is provided. Furthermore, to supply electric source to the electric optical system column 200, an electric optical system control power source is provided.

Next, a transfer mechanism for the glass substrate for imprint 30, 30a to 30c is explained.

The glass substrate for imprint 30, 30a to 30c is transferred from the load port 190 into the mini environment chamber 180, in which alignment work is conducted. Next, the transfer robot for air transfers the glass substrate for imprint 30, 30a to the load lock chamber 162. At the load lock chamber 162, a vacuum pump evacuates the air to make the inside of the load lock chamber 162 a vacuum. When the pressure in the load lock chamber 162 becomes less than or equal to a certain pressure around 1 Pa, the transfer robot for vacuum in the transfer chamber 161 transfers the glass substrate for imprint 30, 30a to 30c from the load lock chamber 162 to the main chamber 160. Then, the glass substrate for imprint 30, 30a to 30c is disposed on the electrostatic chuck on the stage 120.

Then, high-accuracy alignment is performed by using the x, y, z, θ stage 120 and an optical microscope 140. After that, the extraneous substance inspection and pattern defect inspection of the glass substrate for imprint 30, 30a to 30c are conducted by the projection optical system using the electron beam. In the inspection, a surface electric potential is important. To measure the surface electric potential, a surface electric potential measurement device capable of working in a vacuum is provided with the main chamber 160. By measuring a two-dimensional surface electric potential distribution on the sample with the surface electric potential measurement device, a focus control of the second optical system 90 that forms electron image is carried out. A two-dimensional focus map for the glass substrate for imprint 30, 30a to 30c is drawn up on the basis of the two-dimensional surface electric potential distribution, and the inspection is performed by changing and controlling the focus during the inspection. By doing this, blur and distortion of the image due to the surface electric potential change depending on place can be decreased, and the inspection to obtain the high-accuracy and stable image becomes possible.

Thus, according to the embodiments of the present invention, it is possible to provide an inspection method and apparatus of a glass substrate for imprint whereby a fine pattern of a nanometer-level formed on the glass substrate for imprint is inspected with high accuracy.

All examples and conditional language recited herein are intended for pedagogical purposes to aid the reader in understanding the invention and the concepts contributed by the inventor to furthering the art, and are to be construed as being without limitation to such specifically recited examples and conditions, nor does the organization of such examples in the specification relate to a showing of the superiority or inferiority of the invention. Although the embodiments of the present invention have been described in detail, it should be understood that the various changes, substitutions, and alterations could be made hereto without departing from the spirit and scope of the invention.

What is claimed is:

1. A method for inspecting a substrate with a pattern surface for imprint to be transferred to another film, the method comprising: a first alignment step of aligning the substrate in a mini environment chamber by using a substrate alignment device after the substrate has been transferred into the mini environment chamber; a second alignment step of aligning the substrate in a main chamber by using a movable stage and an optical microscope after the substrate has been transferred from the mini environment chamber into the main chamber; an electron beam irradiation step of irradiating the pattern surface of the substrate for imprint disposed on a stage with an electron beam having a predetermined irradiation area, the substrate consisting of a glass substrate made of a single glass material and a transmissive conductive film that transmit light, the glass substrate having the pattern surface of a fine concave-convex configuration pattern, the transmissive conductive film being formed only on a convex part of the fine concave-convex configuration pattern of the glass substrate so as to cover at least a whole surface of the convex part of the concave-convex configuration pattern of the glass substrate; an electron detection step of simultaneously detecting electrons form the pattern surface by the electron beam irradiation by means of a detection surface with a plurality of pixels; and a defect detection step of obtaining an image of the pattern surface based on the electrons detected by the detection surface and detecting a defect of the pattern surface, wherein the electron beam irradiation step includes a first step to irradiate the pattern surface with a first electron beam and a second step to irradiate the pattern surface with a second electron beam with a landing energy less than that of the first electron beam after the first step, wherein a difference between a landing energy of the first electron beam for pre-charge and the landing energy of the second electron beam is 5 to 20 eV, and the landing energy of the first electron beam is 0 to 40 eV, so as to obtain mirror electrons, and wherein a thickness of the transmissive conductive film is smaller than a thickness of the convex part of the concave-convex configuration pattern of the glass substrate.

2. The inspection method as claimed in claim 1, wherein the landing energy of the second beam is greater than or equal to −10 electron volts and is less than or equal to 10 electron volts.

3. The inspection method as claimed in claim 1, wherein the electron detection step is performed by means of a detection surface of an electron beam time delay integration sensor.

4. The inspection method as claimed in claim 1, wherein the defect of the pattern surface detected in the defect detection step includes a pattern defect and/or an attached extraneous substance.

5. An inspection apparatus to inspect a substrate with a pattern surface for imprint to be transferred to another film, the apparatus comprising: a mini environment chamber; a substrate alignment device to perform a first alignment of the substrate included in the mini environment; a main chamber; a movable stage included in the main chamber, an optical microscope to perform a second alignment of the substrate in cooperation with the movable stage in the main chamber, wherein the electro optical system includes an electron gun configured to irradiate the pattern surface of the substrate for imprint disposed on a stage with an electron beam having a predetermined irradiation area, the substrate consisting of a glass substrate made of a single glass material and a transmissive conductive film that transmits light, the glass substrate having the pattern surface of a fine concave-convex configuration pattern, the transmissive conductive film being formed only on a convex part of the fine concave-convex configuration pattern of the glass substrate so as to cover at least a whole surface of the convex part of the concave-convex configuration pattern of the glass substrate; a detector configured to simultaneously detect electrons from the pattern surface by the electron beam irradiation by means of a detection surface with a plurality of pixels; a defect detection unit configured to obtain an image of the pattern surface based on the electrons detected by the detection surface of the detector and to detect a defect of the pattern surface, and a landing energy setting unit configured to set a landing energy of the electron beam so that the electron gun can sequentially irradiate the pattern surface with a first electron beam and with a second electron beam having a landing energy less than that of the first electron beam, wherein a difference between a landing energy of the first electron beam for pre-charged and the landing energy of the second electron beam is 5 to 20 eV, and wherein a thickness of the transmissive conductive film is smaller than a thickness of the convex part of the concave-convex configuration pattern of the glass substrate.

6. The inspection apparatus as claimed in claim 5, wherein the landing energy of the second electron beam is greater than or equal to −10 electron volts and is less than or equal to 10 electron volts.

7. The inspection apparatus as claimed in claim 5, wherein the detector is an electron beam time delay integration sensor.

8. The inspection apparatus as claimed in claim 5, wherein the defect of the pattern surface includes a pattern defect and/or an attached extraneous substance.

9. The inspection method as claimed in claim 1, wherein the transmissive conductive film transmits light in the visible spectrum and the ultraviolet spectrum.

10. The inspection method of claim 9, wherein the transmissive conductive film transmits light having a wavelength of not less than 330 nm.

11. The inspection method as claimed in claim 5, wherein the transmissive conductive film transmits light in the visible spectrum and the ultraviolet spectrum.

12. The inspection method of claim 11, wherein the transmissive conductive film transmits light having a wavelength of not less than 330 nm.

13. The inspection method as claimed in claim 1, wherein a difference between a landing energy of the first electron beam for pre-charge and the landing energy of the second electron beam is 10 to 15 eV.

14. The inspection apparatus as claimed in claim 5, wherein a difference between a landing energy of the first electron beam for pre-charge and the landing energy of the second electron beam is 10 to 15 eV.

15. A method for inspecting a substrate with a pattern surface for imprint to be transferred to another film, the method comprising: an electron beam irradiation step of irradiating the pattern surface of the substrate for imprint disposed on a stage with an electron beam having a predetermined irradiation area, the substrate consisting of a glass substrate made of a single glass material and a transmissive conductive film that transmit light, the glass substrate having the pattern surface of a fine concave-convex configuration pattern, the transmissive conductive film being formed only on a convex part of the fine concave-convex configuration pattern of the glass substrate so as to cover at least a whole surface of the convex part of the concave-convex configuration pattern of the glass substrate; an electron detection step of simultaneously detecting electrons from the pattern surface by the electron beam irradiation by means of a detection surface with a plurality of pixels; and a defect detection step of obtaining an image of the pattern surface based on the electrons detected by the detection surface and detecting a defect of the pattern surface, wherein the electron beam irradiation step includes a first step to irradiate the pattern surface with a first electron beam and a second step to irradiate the pattern surface with a second electron beam with a landing energy less than that of the first electron beam after the first step, wherein a difference between a landing energy of the first electron beam for pre-charge and the landing energy of the second electron beam is 5 to 20 eV, and the landing energy of the first electron beam is 0 to 40 eV, so as to obtain mirror electrons, and wherein a thickness of the transmissive conductive film is smaller than a thickness of the convex part of the concave-convex configuration pattern of the glass substrate.

16. The method as claimed in claim 15,
wherein only the convex part of the concave-convex configuration pattern of the glass substrate is covered with the transmissive conductive film.

17. The method as claimed in claim 15,
wherein the back side of the glass substrate is coated with a transmissive conductive film.

18. The inspection method as claimed in claim 1,
wherein a width of the fine concave-convex configuration pattern of the glass substrate is between 10 and 20 nm, between 10 and 50 nm or between 10 and 100 nm.

19. The inspection apparatus as claimed in claim 5,
wherein a width of the fine concave-convex configuration pattern of the glass substrate is between 10 and 20 nm, between 10 and 50 nm or between 10 and 100 nm.

20. The method as claimed in claim 15,
wherein a width of the fine concave-convex configuration pattern of the glass substrate is between 10 and 20 nm, between 10 and 50 nm or between 10 and 100 nm.

21. The inspection method as claimed in claim 1,
wherein only the convex part of the concave-convex configuration pattern of the glass substrate is covered with the transmissive conductive film.

22. The inspection method as claimed in claim 5,
wherein only the convex part of the concave-convex configuration pattern of the glass substrate is covered with the transmissive conductive film.

* * * * *